(12) United States Patent
Jakobsen et al.

(10) Patent No.: US 8,017,730 B2
(45) Date of Patent: Sep. 13, 2011

(54) T CELL RECEPTORS WHICH SPECIFICALLY BIND TO VYGFVRACL-HLA-A24

(75) Inventors: Bent Karsten Jakobsen, Abingdon (GB); Li Yi, Abingdon (GB)

(73) Assignee: Immunocore Limited, Oxon (GB)

( * ) Notice: Subject to any disclaimer, the term of this patent is extended or adjusted under 35 U.S.C. 154(b) by 269 days.

(21) Appl. No.: 11/915,190

(22) PCT Filed: May 19, 2006

(86) PCT No.: PCT/GB2006/001857
§ 371 (c)(1), (2), (4) Date: Jun. 6, 2008

(87) PCT Pub. No.: WO2006/125962
PCT Pub. Date: Nov. 30, 2006

(65) Prior Publication Data
US 2008/0292602 A1    Nov. 27, 2008

(30) Foreign Application Priority Data

May 25, 2005 (GB) ................. PCT/GB2005/002078
Nov. 30, 2005 (GB) ................................... 0524477.7

(51) Int. Cl.
| C07K 1/00 | (2006.01) |
| C07K 14/00 | (2006.01) |
| C07K 17/00 | (2006.01) |
| C12N 5/071 | (2010.01) |

(52) U.S. Cl. ..................................... 530/350; 435/372.3
(58) Field of Classification Search .................. None
See application file for complete search history.

(56) References Cited

U.S. PATENT DOCUMENTS
2002/0058253 A1 * 5/2002 Kranz et al. ...................... 435/6

FOREIGN PATENT DOCUMENTS
| WO | WO 03020763 A2 * | 3/2003 |
| WO | WO 2004/044004 A2 | 5/2004 |
| WO | WO 2005/116075 A1 | 12/2005 |
| WO | WO 2006/064176 A1 | 6/2006 |

OTHER PUBLICATIONS

Brawley et al., 1999, J. Immunol. vol. 163: 4949-4952.*
Arai et al., "Identification of human telomerase reverse transcriptase-derived peptides that induce HLA-A24-restricted antileukemia cytotoxic T lymphocytes" Blood, vol. 97, No. 9, May 1, 2001, pp. 2903-2907, XP002408551.
Li et al., "Directed evolution of human T-cell receptors with picomolar affinities by phage display" Nature Biotechnology, vol. 23, No. 3, Mar. 2005, pp. 349-354, XP002336795.
Cole et al., "Crystal structure of HLA-A*2402 complexed with a telomerase peptide" European Journal of Immunology, vol. 36, No. 1, Jan. 2006, pp. 170-179, XP002408552.

* cited by examiner

*Primary Examiner* — Amy Juedes
(74) *Attorney, Agent, or Firm* — Banner & Witcoff, Ltd.

(57) ABSTRACT

The present invention provides isolated T cell receptors (TCRs) having the property of specifically binding to the VYGFVRACL (SEQ ID NO:1)-HLA-A24 peptide-MHC. Such TCRs are useful, either alone or associated with a therapeutic agent, for targeting cancerous cells presenting the complex.

1 Claim, 13 Drawing Sheets

Figure 1a

Figure 7A:
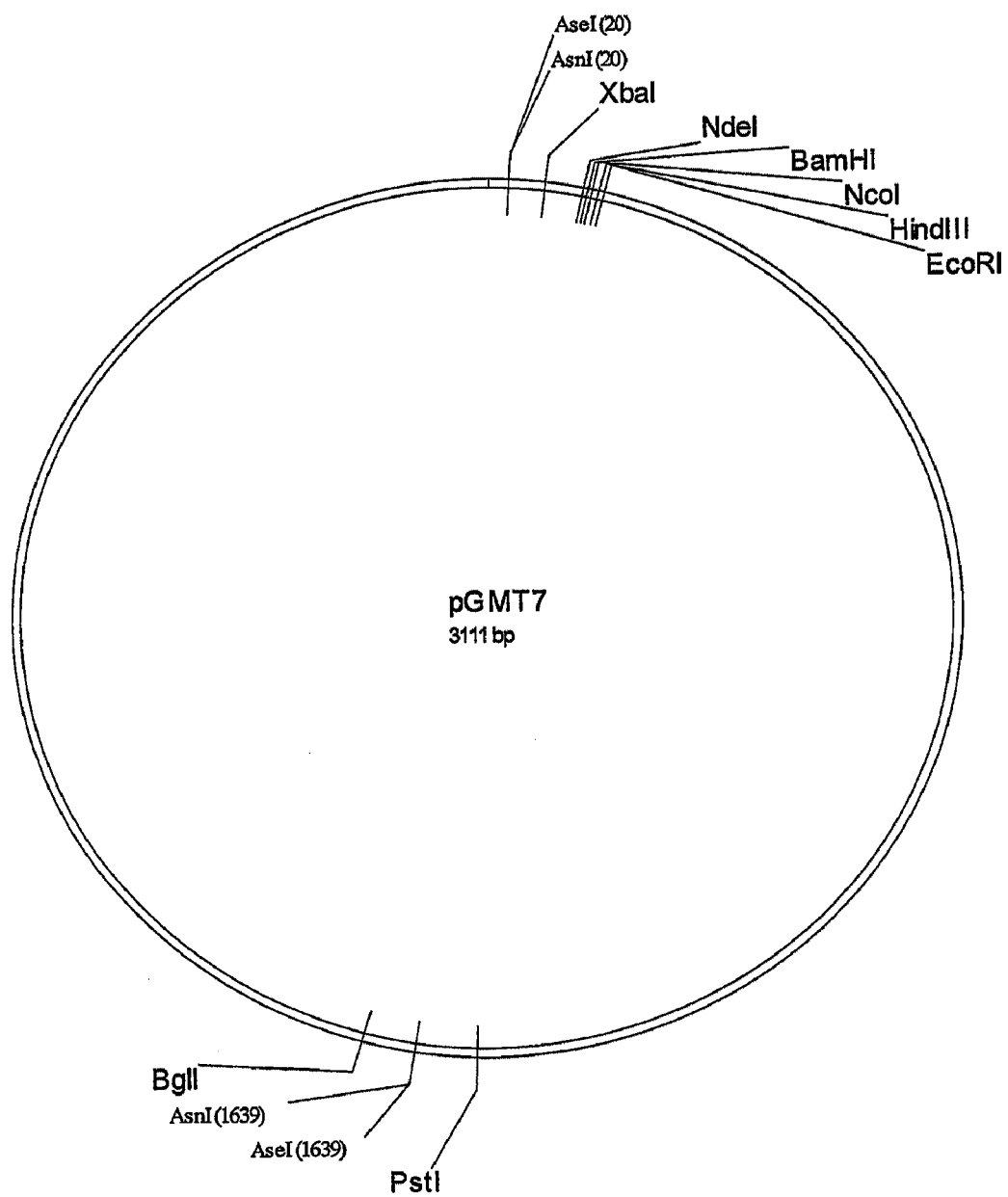

```
              10                    20
               *                     *
M K N Q V E Q S P P D L I L Q E G A N S T L R C N F S D S 30                    40                    50
   *                     *                     *
V N N L Q W F H Q N P W G Q L I N L F Y I P S G T K Q N G 60                    70                    80
   *                     *                     *
R L S A T T V A T E R Y S L L Y I S S S Q T T D S G V Y F 90                    100                   110
   *                     *                     *
C A V D S A T S G T Y K Y I F G T G T R L K V L A N
```
(SEQ ID No: 2)

Figure 1b

```
              10                    20
               *                     *
M N A G V T Q T P K F Q V L K T G Q S M T L Q C A Q D M N 30                    40                    50
     *                     *                     *
H E Y M S W Y R Q D P G M G L R L I H Y S V G A G I T D Q 60                    70                    80
         *                     *                     *
G E V P N G Y N V S R S T T E D F P L R L L S A A P S Q T 90                   100                   110
         *                     *                     *
S V Y F C A A E P S A E G K V Y F G P G T R L T V T
(SEQ ID No: 3)
```

Figure 2a tata<u>catatg</u>aaaaaccaagtggagcagagtcctccagacctgattctccaggagggagccaattccacgctgcggtgcaa
ttttctgactctgtgaacaatttgcagtggtttcatcaaaacccttggggacagctcatcaacctgttttacattccctcagggac
aaaacagaatggaagattaagcgccacgactgtcgctacggaacgctacagcttattgtacatttcctcttcccagaccacag
actcaggcgtttatttctgtgctgtggactctgctacctcaggaacctacaaatacatctttggaacaggcaccaggctgaagg
ttttagcaaatatccagaaccctgaccctgccgtgtaccagctgagagactctaagtcgagtgacaagtctgtctgcctattca
ccgatttgattctcaaacaaatgtgtcacaaagtaaggattctgatgtgtatatcacagacaaaactgtgctagacatgaggtc
tatggacttcaagagcaacagtgctgtggcctggagcaacaaatctgactttgcatgtgcaaacgccttcaacaacagcatta
ttccagaagacaccttcttccccagcccaga<u>aagttcc</u>
(SEQ ID No: 9)

Figure 2b tata<u>catatg</u>aatgctggtgtaactcaaacaccaaaattccaggtcctgaagacaggacagagcatgacactgcagtgtgcc
caggatatgaaccatgaatacatgtcctggtatcgacaagacccaggcatggggctgaggctgattcattactcagttggtgc
tggtatcactgaccaaggagaagtccccaatggctacaatgtctccagatcaaccacagaggatttcccgctcaggctgctg
tcggctgctccctcccagacatctgtgtacttctgtgccgctgagccttctgcggaggggaaggtttacttcgggccgggcac
caggctcacggtcacagaggacctgaaaaacgtgttcccacccgaggtcgctgtgtttgagccatcagaagcagagatctc
ccacacccaaaaggccacactggtgtgcctggccaccggtttctaccccgaccacgtggagctgagctggtgggtgaatg
ggaaggaggtgcacagtggggtcagcacagacccgcagcccctcaaggagcagcccgccctcaatgactccagatacg
ctctgagcagccgcctgagggtctcggccaccttctggcaggaccccgcaaccacttccgctgtcaagtccagttctacg
ggctctcggagaatgacgagtggacccaggatagggccaaacccgtcacccagatcgtcagcgccgaggcctggggta
gagcagact<u>aagctt</u>gaattc
(SEQ ID No: 10)

Figure 3a

```
M K N Q V E Q S P P D L I L Q E G A N S T L R C N F S D S
V N N L Q W F H Q N P W G Q L I N L F Y I P S G T K Q N G
R L S A T T V A T E R Y S L L Y I S S S Q T T D S G V Y F
C A V D S A T S G T Y K Y I F G T G T R L K V L A N I Q N
P D P A V Y Q L R D S K S S D K S V C L F T D F D S Q T N
V S Q S K D S D V Y I T D K T V L D M R S M D F K S N S A
V A W S N K S D F A C A N A F N N S I I P E D T F F P S P
E S S
```
(SEQ ID No: 11)

Figure 3b

```
M N A G V T Q T P K F Q V L K T G Q S M T L Q C A Q D M N
H E Y M S W Y R Q D P G M G L R L I H Y S V G A G I T D Q
G E V P N G Y N V S R S T T E D F P L R L L S A A P S Q T
S V Y F C A A E P S A E G K V Y F G P G T R L T V T E D L
K N V F P P E V A V F E P S E A E I S H T Q K A T L V C L
A T G F Y P D H V E L S W W V N G K E V H S G V S T D P Q
P L K E Q P A L N D S R Y A L S S R L R V S A T F W Q D P
R N H F R C Q V Q F Y G L S E N D E W T Q D R A K P V T Q
I V S A E A W G R A D
```
(SEQ ID No: 12)

Figure 4a tata<u>catatg</u>aaaaaaccaagtggagcagagtcctccagacctgattctccaggagggagccaattccacgctgcggtgcaa tttttctgactctgtgaacaatttgcagtggtttcatcaaaacccttggggacagctcatcaacctgttttacattccctcagggac aaaacagaatggaagattaagcgccacgactgtcgctacggaacgctacagcttattgtacatttcctcttcccagaccacag actcaggcgtttatttctgtgctgtggactctgctacctcaggaacctacaaatacatctttggaacaggcaccaggctgaagg ttttagcaaatatccagaaccctgaccctgccgtgtaccagctgagagactctaagtcgagtgacaagtctgtctgcctattca ccgattttgattctcaaacaaatgtgtcacaaagtaaggattctgatgtgtatatcacagacaaa<u>tgt</u>gtgctagacatgaggtc tatggacttcaagagcaacagtgctgtggcctggagcaacaaatctgactttgcatgtgcaaacgccttcaacaacagcatta ttccagaagacaccttcttccccagcccaga<u>aagttcc</u>

(SEQ ID No: 13)

Figure 4b tata<u>catatg</u>aatgctggtgtaactcaaacaccaaaattccaggtcctgaagacaggacagagcatgacactgcagtgtgcc
caggatatgaaccatgaatacatgtcctggtatcgacaagacccaggcatggggctgaggctgattcattactcagttggtgc
tggtatcactgaccaaggagaagtccccaatggctacaatgtctccagatcaaccacagaggatttcccgctcaggctgctg
tcggctgctccctcccagacatctgtgtacttctgtgccgctgagccttctgcggaggggaaggtttacttcgggccgggcac
caggctcacggtcacagaggacctgaaaaacgtgttcccacccgaggtcgctgtgtttgagccatcagaagcagagatctc
ccacacccaaaaggccacactggtgtgcctggccaccggtttctaccccgaccacgtggagctgagctggtgggtgaatg
ggaaggaggtgcacagtggggtc<u>tgc</u>acagacccgcagcccctcaaggagcagcccgccctcaatgactccagatacg
ctctgagcagccgcctgagggtctcggccaccttctggcaggaccccgcaaccacttccgctgtcaagtccagttctacg
ggctctcggagaatgacgagtggacccaggatagggccaaacccgtcacccagatcgtcagcgccgaggcctggggta
gagcagact<u>aagctt</u>gaattc (SEQ ID No: 14)

Figure 5a

```
M K N Q V E Q S P P D L I L Q E G A N S T L R C N F S D S
V N N L Q W F H Q N P W G Q L I N L F Y I P S G T K Q N G
R L S A T T V A T E R Y S L L Y I S S S Q T T D S G V Y F
C A V D S A T S G T Y K Y I F G T G T R L K V L A N I Q N
P D P A V Y Q L R D S K S S D K S V C L F T D F D S Q T N
V S Q S K D S D V Y I T D K C V L D M R S M D F K S N S A
V A W S N K S D F A C A N A F N N S I I P E D T F F P S P
E S S
```
(SEQ ID No: 15)

Figure 5b

```
M N A G V T Q T P K F Q V L K T G Q S M T L Q C A Q D M N
H E Y M S W Y R Q D P G M G L R L I H Y S V G A G I T D Q
G E V P N G Y N V S R S T T E D F P L R L L S A A P S Q T
S V Y F C A A E P S A E G K V Y F G P G T R L T V E D L
K N V F P P E V A V F E P S E A E I S H T Q K A T L V C L
A T G F Y P D H V E L S W W V N G K E V H S G V C T D P Q
P L K E Q P A L N D S R Y A L S S R L R V S A T F W Q D P
R N H F R C Q V Q F Y G L S E N D E W T Q D R A K P V T Q
I V S A E A W G R A D
```
(SEQ ID No: 16)

Figure 6a

I Q N P D P A V Y Q L R D S K S S D K S V C L F T
D F D S Q T N V S Q S K D S D V Y I T D K
(SEQ ID No: 4)

Figure 6b

E D L N K V F P P E V A V F E P S E A E I S H T Q K A T
L V C L A T G F F P D H V E L S W W V N G K E V H S G V
(SEQ ID No: 5)

Figure 6c

E D L K N V F P P E V A V F E P S E A E I S H T Q K A T
L V C L A T G F Y P D H V E L S W W V N G K E V H S G V
(SEQ ID No: 6)

Figure 7b

```
   1 GATCTCGATC CCGCGAAATT AATACGACTC ACTATAGGGA GACCACAACG
  51 GTTTCCCTCT AGAAATAATT TTGTTTAACT TTAAGAAGGA GATATACATA
 101 TGGGATCCAT GGTAAGCTTG AATTCCGATC CGGCTGCTAA CAAAGCCCGA
 151 AAGGAAGCTG AGTTGGCTGC TGCCACCGCT GAGCAATAAC TAGCATAACC
 201 CCTTGGGGCC TCTAAACGGG TCTTGAGGGG TTTTTTGCTG AAAGGAGGAA
 251 CTATATCCGG ATAATTCTTG AAGACGAAAG GGCCTCGTGA TACGCCTATT
 301 TTTATAGGTT AATGTCATGA TAATAATGGT TTCTTAGACG TCAGGTGGCA
 351 CTTTTCGGGG AAATGTGCGC GGAACCCCTA TTTGTTTATT TTTCTAAATA
 401 CATTCAAATA TGTATCCGCT CATGAGACAA TAACCCTGAT AAATGCTTCA
 451 ATAATATTTT GTTAAAATTC GCGTTAAATT TTTGTTAAAT CAGCTCATTT
 501 TTTAACCAAT AGGCCGAAAT CGGCAAAATC CCTTATAAAT CAAAAGAATA
 551 GACCGAGATA GGGTTGAGTG TTGTTCCAGT TTGGAACAAG AGTCCACTAT
 601 TAAAGAACGT GGACTCCAAC GTCAAAGGGC GAAAAACCGT CTATCAGGGC
 651 GATGGCCCAC TACGTGAACC ATCACCCTAA TCAAGTTTTT TGGGGTCGAG
 701 GTGCCGTAAA GCACTAAATC GGAACCCTAA AGGGAGCCCC CGATTTAGAG
 751 CTTGACGGGG AAAGCCGGCG AACGTGGCGA GAAAGGAAGG GAAGAAAGCG
 801 AAAGGAGCGG CGCTAGGGC GCTGGCAAGT GTAGCGGTCA CGCTGCGCGT
 851 AACCACCACA CCCGCCGCGC TTAATGCGCC GCTACAGGGC GCGTCAGGTG
 901 GCACTTTTCG GGGAAATGTG CGCGGAACCC CTATTTGTTT ATTTTTCTAA
 951 ATACATTCAA ATATGTATCC GCTCATGAGA CAATAACCCT GATAAATGCT
1001 TCAATAATAT TGAAAAGGA AGAGTATGAG TATTCAACAT TTCCGTGTCG
1051 CCCTTATTCC CTTTTTTGCG GCATTTTGCC TTCCTGTTTT TGCTCACCCA
1101 GAAACGCTGG TGAAAGTAAA AGATGCTGAA GATCAGTTGG GTGCACGAGT
1151 GGGTTACATC GAACTGGATC TCAACAGCGG TAAGATCCTT GAGAGTTTTC
1201 GCCCCGAAGA ACGTTTTCCA ATGATGAGCA CTTTTAAAGT TCTGCTATGT
1251 GGCGCGGTAT TATCCCGTGT TGACGCCGGG CAAGAGCAAC TCGGTCGCCG
1301 CATACACTAT TCTCAGAATG ACTTGGTTGA GTACTCACCA GTCACAGAAA
1351 AGCATCTTAC GGATGGCATG ACAGTAAGAG AATTATGCAG TGCTGCCATA
1401 ACCATGAGTG ATAACACTGC GGCCAACTTA CTTCTGACAA CGATCGGAGG
1451 ACCGAAGGAG CTAACCGCTT TTTTGCACAA CATGGGGGAT CATGTAACTC
1501 GCCTTGATCG TTGGGAACCG GAGCTGAATG AAGCCATACC AAACGACGAG
1551 CGTGACACCA CGATGCCTGC AGCAATGGCA ACAACGTTGC GCAAACTATT
1601 AACTGGCGAA CTACTTACTC TAGCTTCCCG GCAACAATTA ATAGACTGGA
1651 TGGAGGCGGA TAAAGTTGCA GGACCACTTC TGCGCTCGGC CCTTCCGGCT
1701 GGCTGGTTTA TTGCTGATAA ATCTGGAGCC GGTGAGCGTG GTCTCGCGG
1751 TATCATTGCA GCACTGGGGC CAGATGGTAA GCCCTCCCGT ATCGTAGTTA
1801 TCTACACGAC GGGGAGTCAG GCAACTATGG ATGAACGAAA TAGACAGATC
1851 GCTGAGATAG GTGCCTCACT GATTAAGCAT TGGTAACTGT CAGACCAAGT
1901 TTACTCATAT ATACTTTAGA TTGATTTAAA ACTTCATTTT TAATTTAAAA
1951 GGATCTAGGT GAAGATCCTT TTTGATAATC TCATGACCAA AATCCCTTAA
2001 CGTGAGTTTT CGTTCCACTG AGCGTCAGAC CCCGTAGAAA AGATCAAAGG
2051 ATCTTCTTGA GATCCTTTTT TTCTGCGCGT AATCTGCTGC TTGCAAACAA
```

Figure 7b (Cont.)

```
2101  AAAAACCACC GCTACCAGCG GTGGTTTGTT TGCCGGATCA AGAGCTACCA
2151  ACTCTTTTTC CGAAGGTAAC TGGCTTCAGC AGAGCGCAGA TACCAAATAC
2201  TGTCCTTCTA GTGTAGCCGT AGTTAGGCCA CCACTTCAAG AACTCTGTAG
2251  CACCGCCTAC ATACCTCGCT CTGCTAATCC TGTTACCAGT GGCTGCTGCC
2301  AGTGGCGATA AGTCGTGTCT TACCGGGTTG GACTCAAGAC GATAGTTACC
2351  GGATAAGGCG CAGCGGTCGG GCTGAACGGG GGGTTCGTGC ACACAGCCCA
2401  GCTTGGAGCG AACGACCTAC ACCGAACTGA GATACCTACA GCGTGAGCTA
2451  TGAGAAAGCG CCACGCTTCC CGAAGGGAGA AAGGCGGACA GGTATCCGGT
2501  AAGCGGCAGG GTCGGAACAG GAGAGCGCAC GAGGGAGCTT CCAGGGGGAA
2551  ACGCCTGGTA TCTTTATAGT CCTGTCGGGT TTCGCCACCT CTGACTTGAG
2601  CGTCGATTTT TGTGATGCTC GTCAGGGGGG CGGAGCCTAT GGAAAAACGC
2651  CAGCAACGCG GCCTTTTTAC GGTTCCTGGC CTTTTGCTGG CCTTTTGCTC
2701  ACATGTTCTT TCCTGCGTTA TCCCCTGATT CTGTGGATAA CCGTATTACC
2751  GCCTTTGAGT GAGCTGATAC CGCTCGCCGC AGCCGAACGA CCGAGCGCAG
2801  CGAGTCAGTG AGCGAGGAAG CGGAAGAGCG CCTGATGCGG TATTTCTCC
2851  TTACGCATCT GTGCGGTATT TCACACCGCA ATGGTGCACT CTCAGTACAA
2901  TCTGCTCTGA TGCCGCATAG TTAAGCCAGT ATACACTCCG CTATCGCTAC
2951  GTGACTGGGT CATGGCTGCG CCCCGACACC CGCCAACACC CGCTGACGCG
3001  CCCTGACGGG CTTGTCTGCT CCCGGCATCC GCTTACAGAC AAGCTGTGAC
3051  CGTCTCCGGG AGCTGCATGT GTCAGAGGTT TTCACCGTCA TCACCGAAAC
3101  GCGCGAGGCA G
```
(SEQ ID NO: 17)

Figure 8

```
M N A G V T Q T P K F Q V L K T G Q S M T L Q C A Q D M N
H E Y M S W Y R Q D P G M G L R L I H Y S V G A G I T D Q
G E V P N G Y N V S R S T T E D F P L R L L S A A P S Q T
S V Y F C A A E P S A E G K V Y F G P G T R L T V T E D L
K N V F P P E V A V F E P S E A E I S H T Q K A T L V C L
A T G F Y P D H V E L S W W V N G K E V H S G V C T D P Q
P L K E Q P A L N D S R Y A L S S R L R V S A T F W Q D P
R N H F R C Q V Q F Y G L S E N D E W T Q D R A K P V T Q
I V S A E A W G R A D P G A P T S S S T K K T Q L Q L E H
L L L D L Q M I L N G I N N Y K N P K L T R M L T F K F Y
M P K K A T E L K H L Q C L E E E L K P L E E V L N L A Q
S K N F H L R P R D L I S N I N V I V L E L K G S E T T F
M C E Y A D E T A T I V E F L N R W I T F C Q S I I S T L
T
```
(SEQ ID NO: 18)

Figure 10a

MQKEVEQNSGPLSVPEGAIASLNCTYSDRGSQSFFWYRQYSGKSPELIMSIYSN
GDKEDGRFTAQLNKASQYVSLLTRDSQPSDSATYLCAQSQCTENQFGAGTQV
VVTPD
(SEQ ID NO: 19)

Figure 10b

MQKEVEQNSGPLSVPEGAIASLNCTYS<u>DRGSQS</u>FFWYRQYSGKSPELIMS<u>IY</u>SN
GDKEDGRFTAQLNKASQYVSLLTRDSQPSDSATYL<u>CAQS</u>QCTENQFGAGTQV
VVTPDIQNPDPAVYQLRDSKSSDKSVCLFTDFDSQTNVSQSKDSDVYITDKSV
LDMRSMDFKSNSAVAWSNKSDFACANAFNNSIIPEDTFFPSPESS
(SEQ ID NO: 20)

SEQUENCE LISTING

```
<160> NUMBER OF SEQ ID NOS: 22

<210> SEQ ID NO 1
<211> LENGTH: 9
<212> TYPE: PRT
<213> ORGANISM: Homo sapiens

<400> SEQUENCE: 1

Val Tyr Gly Phe Val Arg Ala Cys Leu
 1               5

<210> SEQ ID NO 2
<211> LENGTH: 113
<212> TYPE: PRT
<213> ORGANISM: Artificial Sequence
<220> FEATURE:
<223> OTHER INFORMATION: Recombinant VYG TCR alpha chain variable
      region

<400> SEQUENCE: 2

Met Lys Asn Gln Val Glu Gln Ser Pro Pro Asp Leu Ile Leu Gln Glu
 1               5                  10                  15

Gly Ala Asn Ser Thr Leu Arg Cys Asn Phe Ser Asp Ser Val Asn Asn
                20                  25                  30

Leu Gln Trp Phe His Gln Asn Pro Trp Gly Gln Leu Ile Asn Leu Phe
            35                  40                  45

Tyr Ile Pro Ser Gly Thr Lys Gln Asn Gly Arg Leu Ser Ala Thr Thr
        50                  55                  60

Val Ala Thr Glu Arg Tyr Ser Leu Leu Tyr Ile Ser Ser Ser Gln Thr
65                  70                  75                  80

Thr Asp Ser Gly Val Tyr Phe Cys Ala Val Asp Ser Ala Thr Ser Gly
                85                  90                  95

Thr Tyr Lys Tyr Ile Phe Gly Thr Gly Thr Arg Leu Lys Val Leu Ala
               100                 105                 110

Asn

<210> SEQ ID NO 3
<211> LENGTH: 113
<212> TYPE: PRT
<213> ORGANISM: Artificial Sequence
<220> FEATURE:
<223> OTHER INFORMATION: Recombinant VYG TCR beta chain variable
      region

<400> SEQUENCE: 3

Met Asn Ala Gly Val Thr Gln Thr Pro Lys Phe Gln Val Leu Lys Thr
```

```
            1               5                  10                 15
Gly Gln Ser Met Thr Leu Gln Cys Ala Gln Asp Met Asn His Glu Tyr
                 20                 25                 30

Met Ser Trp Tyr Arg Gln Asp Pro Gly Met Gly Leu Arg Leu Ile His
             35                 40                 45

Tyr Ser Val Gly Ala Gly Ile Thr Asp Gln Gly Glu Val Pro Asn Gly
         50                 55                 60

Tyr Asn Val Ser Arg Ser Thr Thr Glu Asp Phe Pro Leu Arg Leu Leu
 65                 70                 75                 80

Ser Ala Ala Pro Ser Gln Thr Ser Val Tyr Phe Cys Ala Ala Glu Pro
                 85                 90                 95

Ser Ala Glu Gly Lys Val Tyr Phe Gly Pro Gly Thr Arg Leu Thr Val
             100                105                110

Thr
```

```
<210> SEQ ID NO 4
<211> LENGTH: 46
<212> TYPE: PRT
<213> ORGANISM: Homo sapiens

<400> SEQUENCE: 4

Ile Gln Asn Pro Asp Pro Ala Val Tyr Gln Leu Arg Asp Ser Lys Ser
 1               5                  10                 15

Ser Asp Lys Ser Val Cys Leu Phe Thr Asp Phe Asp Ser Gln Thr Asn
                 20                 25                 30

Val Ser Gln Ser Lys Asp Ser Asp Val Tyr Ile Thr Asp Lys
             35                 40                 45
```

```
<210> SEQ ID NO 5
<211> LENGTH: 56
<212> TYPE: PRT
<213> ORGANISM: Homo sapiens

<400> SEQUENCE: 5

Glu Asp Leu Asn Lys Val Phe Pro Pro Glu Val Ala Val Phe Glu Pro
 1               5                  10                 15

Ser Glu Ala Glu Ile Ser His Thr Gln Lys Ala Thr Leu Val Cys Leu
                 20                 25                 30

Ala Thr Gly Phe Phe Pro Asp His Val Glu Leu Ser Trp Trp Val Asn
             35                 40                 45

Gly Lys Glu Val His Ser Gly Val
         50                 55
```

```
<210> SEQ ID NO 6
<211> LENGTH: 56
<212> TYPE: PRT
<213> ORGANISM: Homo sapiens

<400> SEQUENCE: 6

Glu Asp Leu Lys Asn Val Phe Pro Pro Glu Val Ala Val Phe Glu Pro
 1               5                  10                 15

Ser Glu Ala Glu Ile Ser His Thr Gln Lys Ala Thr Leu Val Cys Leu
                 20                 25                 30

Ala Thr Gly Phe Tyr Pro Asp His Val Glu Leu Ser Trp Trp Val Asn
             35                 40                 45

Gly Lys Glu Val His Ser Gly Val
         50                 55
```

```
<210> SEQ ID NO 7
<211> LENGTH: 30
<212> TYPE: PRT
<213> ORGANISM: Artificial Sequence
<220> FEATURE:
<223> OTHER INFORMATION: short scTCR linker

<400> SEQUENCE: 7

Pro Gly Gly Gly Ser Gly Gly Gly Ser Gly Gly Gly Ser Gly
 1               5                  10                  15

Gly Gly Gly Ser Gly Gly Gly Gly Ser Gly Gly Gly Gly Pro
            20                  25                  30

<210> SEQ ID NO 8
<211> LENGTH: 35
<212> TYPE: PRT
<213> ORGANISM: Artificial Sequence
<220> FEATURE:
<223> OTHER INFORMATION: Long scTCR linker

<400> SEQUENCE: 8

Pro Gly Gly Gly Ser Gly Gly Gly Ser Gly Gly Gly Ser Gly
 1               5                  10                  15

Gly Gly Gly Ser Gly Gly Gly Gly Ser Gly Gly Gly Ser Gly Gly
            20                  25                  30

Gly Gly Pro
        35

<210> SEQ ID NO 9
<211> LENGTH: 625
<212> TYPE: DNA
<213> ORGANISM: Artificial Sequence
<220> FEATURE:
<223> OTHER INFORMATION: DNA encoding a truncated recombinant VYG TCR
      alpha chain including restriction enzyme recognition sequences

<400> SEQUENCE: 9
tatacatatg aaaaaccaag tggagcagag tcctccagac ctgattctcc aggagggagc      60
caattccacg ctgcggtgca atttttctga ctctgtgaac aatttgcagt ggtttcatca     120
aaacccttgg ggacagctca tcaacctgtt ttacattccc tcaggacaa aacagaatgg     180 aagattaagc gccacgactg tcgctacgga acgctacagc ttattgtaca tttcctcttc     240
ccagaccaca gactcaggcg tttatttctg tgctgtggac tctgctacct caggaaccta     300
caaatacatc tttggaacag gcaccaggct gaaggtttta gcaaatatcc agaaccctga     360
ccctgccgtg taccagctga gagactctaa gtcgagtgac aagtctgtct gcctattcac     420
cgattttgat tctcaaacaa atgtgtcaca agtaaggat tctgatgtgt atatcacaga     480
caaaactgtg ctagacatga ggtctatgga cttcaagagc aacagtgctg tggcctggag     540
caacaaatct gactttgcat gtgcaaacgc cttcaacaac agcattattc agaagacac     600 cttcttcccc agcccagaaa gttcc                                          625

<210> SEQ ID NO 10
<211> LENGTH: 749
<212> TYPE: DNA
<213> ORGANISM: Artificial Sequence
<220> FEATURE:
<223> OTHER INFORMATION: DNA encoding a truncated recombinant VYG TCR
      beta chain including restriction enzyme recognition sequences

<400> SEQUENCE: 10
tatacatatg aatgctggtg taactcaaac accaaaattc caggtcctga agacaggaca      60
```

```
gagcatgaca ctgcagtgtg cccaggatat gaaccatgaa acatgtcct ggtatcgaca      120 agacccaggc atggggctga ggctgattca ttactcagtt ggtgctggta tcactgacca      180
aggagaagtc cccaatggct acaatgtctc cagatcaacc acagaggatt cccgctcag       240 gctgctgtcg gctgctccct cccagacatc tgtgtacttc tgtgccgctg agccttctgc      300 ggagggaag gtttacttcg ggccgggcac caggctcacg gtcacagagg acctgaaaaa       360
cgtgttccca cccgaggtcg ctgtgtttga gccatcagaa gcagagatct cccacaccca      420
aaaggccaca ctggtgtgcc tggccaccgg tttctacccc gaccacgtgg agctgagctg      480
gtgggtgaat gggaaggagg tgcacagtgg ggtcagcaca gacccgcagc ccctcaagga     540
gcagcccgcc ctcaatgact ccagatacgc tctgagcagc cgcctgaggg tctcggccac      600
cttctggcag acccccgca accacttccg ctgtcaagtc cagttctacg ggctctcgga      660
gaatgacgag tggacccagg ataggggccaa acccgtcacc cagatcgtca gcgccgaggc      720
ctggggtaga gcagactaag cttgaattc                                         749

<210> SEQ ID NO 11
<211> LENGTH: 206
<212> TYPE: PRT
<213> ORGANISM: Artificial Sequence
<220> FEATURE:
<223> OTHER INFORMATION: A truncated recombinant VYG TCR alpha chain

<400> SEQUENCE: 11

Met Lys Asn Gln Val Glu Gln Ser Pro Pro Asp Leu Ile Leu Gln Glu
  1               5                  10                  15

Gly Ala Asn Ser Thr Leu Arg Cys Asn Phe Ser Asp Ser Val Asn Asn
                 20                  25                  30

Leu Gln Trp Phe His Gln Asn Pro Trp Gly Gln Leu Ile Asn Leu Phe
             35                  40                  45

Tyr Ile Pro Ser Gly Thr Lys Gln Asn Gly Arg Leu Ser Ala Thr Thr
 50                  55                  60

Val Ala Thr Glu Arg Tyr Ser Leu Leu Tyr Ile Ser Ser Ser Gln Thr
 65                  70                  75                  80

Thr Asp Ser Gly Val Tyr Phe Cys Ala Val Asp Ser Ala Thr Ser Gly
                 85                  90                  95

Thr Tyr Lys Tyr Ile Phe Gly Thr Gly Thr Arg Leu Lys Val Leu Ala
            100                 105                 110

Asn Ile Gln Asn Pro Asp Pro Ala Val Tyr Gln Leu Arg Asp Ser Lys
            115                 120                 125

Ser Ser Asp Lys Ser Val Cys Leu Phe Thr Asp Phe Asp Ser Gln Thr
130                 135                 140

Asn Val Ser Gln Ser Lys Asp Ser Asp Val Tyr Ile Thr Asp Lys Thr
145                 150                 155                 160

Val Leu Asp Met Arg Ser Met Asp Phe Lys Ser Asn Ser Ala Val Ala
                165                 170                 175

Trp Ser Asn Lys Ser Asp Phe Ala Cys Ala Asn Ala Phe Asn Asn Ser
            180                 185                 190

Ile Ile Pro Glu Asp Thr Phe Phe Pro Ser Pro Glu Ser Ser
            195                 200                 205

<210> SEQ ID NO 12
<211> LENGTH: 243
<212> TYPE: PRT
<213> ORGANISM: Artificial Sequence
<220> FEATURE:
<223> OTHER INFORMATION: A truncated recombinant VYG TCR beta chain
```

<400> SEQUENCE: 12

| Met | Asn | Ala | Gly | Val | Thr | Gln | Thr | Pro | Lys | Phe | Gln | Val | Leu | Lys | Thr |
| 1 | | | | 5 | | | | | 10 | | | | | 15 | |

| Gly | Gln | Ser | Met | Thr | Leu | Gln | Cys | Ala | Gln | Asp | Met | Asn | His | Glu | Tyr |
| | | | 20 | | | | | 25 | | | | | 30 | | |

| Met | Ser | Trp | Tyr | Arg | Gln | Asp | Pro | Gly | Met | Gly | Leu | Arg | Leu | Ile | His |
| | | 35 | | | | | 40 | | | | | 45 | | | |

| Tyr | Ser | Val | Gly | Ala | Gly | Ile | Thr | Asp | Gln | Gly | Glu | Val | Pro | Asn | Gly |
| | 50 | | | | | 55 | | | | | 60 | | | | |

| Tyr | Asn | Val | Ser | Arg | Ser | Thr | Thr | Glu | Asp | Phe | Pro | Leu | Arg | Leu | Leu |
| 65 | | | | | 70 | | | | | 75 | | | | | 80 |

| Ser | Ala | Ala | Pro | Ser | Gln | Thr | Ser | Val | Tyr | Phe | Cys | Ala | Ala | Glu | Pro |
| | | | | 85 | | | | | 90 | | | | | 95 | |

| Ser | Ala | Glu | Gly | Lys | Val | Tyr | Phe | Gly | Pro | Gly | Thr | Arg | Leu | Thr | Val |
| | | | 100 | | | | | 105 | | | | | 110 | | |

| Thr | Glu | Asp | Leu | Lys | Asn | Val | Phe | Pro | Pro | Glu | Val | Ala | Val | Phe | Glu |
| | | | 115 | | | | | 120 | | | | | 125 | | |

| Pro | Ser | Glu | Ala | Glu | Ile | Ser | His | Thr | Gln | Lys | Ala | Thr | Leu | Val | Cys |
| | 130 | | | | | 135 | | | | | 140 | | | | |

| Leu | Ala | Thr | Gly | Phe | Tyr | Pro | Asp | His | Val | Glu | Leu | Ser | Trp | Trp | Val |
| 145 | | | | | 150 | | | | | 155 | | | | | 160 |

| Asn | Gly | Lys | Glu | Val | His | Ser | Gly | Val | Ser | Thr | Asp | Pro | Gln | Pro | Leu |
| | | | | 165 | | | | | 170 | | | | | 175 | |

| Lys | Glu | Gln | Pro | Ala | Leu | Asn | Asp | Ser | Arg | Tyr | Ala | Leu | Ser | Ser | Arg |
| | | | 180 | | | | | 185 | | | | | 190 | | |

| Leu | Arg | Val | Ser | Ala | Thr | Phe | Trp | Gln | Asp | Pro | Arg | Asn | His | Phe | Arg |
| | | 195 | | | | | 200 | | | | | 205 | | | |

| Cys | Gln | Val | Gln | Phe | Tyr | Gly | Leu | Ser | Glu | Asn | Asp | Glu | Trp | Thr | Gln |
| | 210 | | | | | 215 | | | | | 220 | | | | |

| Asp | Arg | Ala | Lys | Pro | Val | Thr | Gln | Ile | Val | Ser | Ala | Glu | Ala | Trp | Gly |
| 225 | | | | | 230 | | | | | 235 | | | | | 240 |

| Arg | Ala | Asp |
| | | |

<210> SEQ ID NO 13
<211> LENGTH: 625
<212> TYPE: DNA
<213> ORGANISM: Artificial Sequence
<220> FEATURE:
<223> OTHER INFORMATION: DNA encoding a truncated recombinant VYG TCR
    alpha chain including an introduced cysteine codon and
    restriction enzyme recognition sequences

<400> SEQUENCE: 13

```
tatacatatg aaaaaccaag tggagcagag tcctccagac ctgattctcc aggagggagc    60
caattccacg ctgcggtgca atttttctga ctctgtgaac aatttgcagt ggtttcatca   120
aaacccttgg ggacagctca tcaacctgtt ttacattccc tcaggacaa aacagaatgg    180
aagattaagc gccacgactg tcgctacgga acgctacagc ttattgtaca tttcctcttc   240
ccagaccaca gactcaggcg tttatttctg tgctgtggac tctgctacct caggaaccta   300
caaatacatc tttggaacag gcaccaggct gaaggtttta gcaaatatcc agaaccctga   360
ccctgccgtg taccagctga gagactctaa gtcgagtgac aagtctgtct gcctattcac   420
cgattttgat tctcaaacaa atgtgtcaca agtaaggat tctgatgtgt atatcacaga    480
caaatgtgtg ctagacatga ggtctatgga cttcaagagc aacagtgctg tggcctggag   540
```

```
caacaaatct gactttgcat gtgcaaacgc cttcaacaac agcattattc cagaagacac    600
cttcttcccc agcccagaaa gttcc                                          625
```

<210> SEQ ID NO 14
<211> LENGTH: 749
<212> TYPE: DNA
<213> ORGANISM: Artificial Sequence
<220> FEATURE:
<223> OTHER INFORMATION: DNA encoding a truncated recombinant VYG TCR
      beta chain including an introduced cysteine codon and restriction
      enzyme recognition sequences

<400> SEQUENCE: 14

```
tatacatatg aatgctggtg taactcaaac accaaaattc caggtcctga agacaggaca     60
gagcatgaca ctgcagtgtg cccaggatat gaaccatgaa tacatgtcct ggtatcgaca    120
agacccaggc atgggctga ggctgattca ttactcagtt ggtgctggta tcactgacca    180
aggagaagtc cccaatggct acaatgtctc cagatcaacc acagaggatt cccgctcag    240 gctgctgtcg gctgctccct cccagacatc tgtgtacttc tgtgccgctg agccttctgc    300
ggaggggaag gtttacttcg gccgggcac caggctcacg gtcacagagg acctgaaaaa    360
cgtgttccca cccgaggtcg ctgtgtttga gccatcagaa gcagagatct cccacaccca    420
aaaggccaca ctggtgtgcc tggccaccgg tttctacccc gaccacgtgg agctgagctg    480
gtgggtgaat gggaaggagg tgcacagtgg ggtctgcaca gacccgcagc ccctcaagga    540
gcagcccgcc ctcaatgact ccagatacgc tctgagcagc cgcctgaggg tctcggccac    600
cttctggcag gaccccgca accacttccg ctgtcaagtc cagttctacg gctctcgga     660 gaatgacgag tggacccagg atagggccaa accccgtcacc cagatcgtca gcgccgaggc    720
ctggggtaga gcagactaag cttgaattc                                      749
```

<210> SEQ ID NO 15
<211> LENGTH: 206
<212> TYPE: PRT
<213> ORGANISM: Artificial Sequence
<220> FEATURE:
<223> OTHER INFORMATION: DNA encoding a truncated recombinant VYG TCR
      alpha chain including an introduced cysteine residue

<400> SEQUENCE: 15

```
Met Lys Asn Gln Val Glu Gln Ser Pro Pro Asp Leu Ile Leu Gln Glu
 1               5                  10                  15

Gly Ala Asn Ser Thr Leu Arg Cys Asn Phe Ser Asp Ser Val Asn Asn
            20                  25                  30

Leu Gln Trp Phe His Gln Asn Pro Trp Gly Gln Leu Ile Asn Leu Phe
        35                  40                  45

Tyr Ile Pro Ser Gly Thr Lys Gln Asn Gly Arg Leu Ser Ala Thr Thr
    50                  55                  60

Val Ala Thr Glu Arg Tyr Ser Leu Leu Tyr Ile Ser Ser Ser Gln Thr
65                  70                  75                  80

Thr Asp Ser Gly Val Tyr Phe Cys Ala Val Asp Ser Ala Thr Ser Gly
                85                  90                  95

Thr Tyr Lys Tyr Ile Phe Gly Thr Gly Thr Arg Leu Lys Val Leu Ala
            100                 105                 110

Asn Ile Gln Asn Pro Asp Pro Ala Val Tyr Gln Leu Arg Asp Ser Lys
        115                 120                 125

Ser Ser Asp Lys Ser Val Cys Leu Phe Thr Asp Phe Asp Ser Gln Thr
    130                 135                 140
```

```
Asn Val Ser Gln Ser Lys Asp Ser Asp Val Tyr Ile Thr Asp Lys Cys
145                 150                 155                 160

Val Leu Asp Met Arg Ser Met Asp Phe Lys Ser Asn Ser Ala Val Ala
                165                 170                 175

Trp Ser Asn Lys Ser Asp Phe Ala Cys Ala Asn Ala Phe Asn Asn Ser
            180                 185                 190

Ile Ile Pro Glu Asp Thr Phe Phe Pro Ser Pro Glu Ser Ser
        195                 200                 205

<210> SEQ ID NO 16
<211> LENGTH: 243
<212> TYPE: PRT
<213> ORGANISM: Artificial Sequence
<220> FEATURE:
<223> OTHER INFORMATION: DNA encoding a truncated recombinant VYG TCR
      beta chain including an introduced cysteine residue

<400> SEQUENCE: 16

Met Asn Ala Gly Val Thr Gln Thr Pro Lys Phe Gln Val Leu Lys Thr
1               5                   10                  15

Gly Gln Ser Met Thr Leu Gln Cys Ala Gln Asp Met Asn His Glu Tyr
                20                  25                  30

Met Ser Trp Tyr Arg Gln Asp Pro Gly Met Gly Leu Arg Leu Ile His
            35                  40                  45

Tyr Ser Val Gly Ala Gly Ile Thr Asp Gln Gly Glu Val Pro Asn Gly
    50                  55                  60

Tyr Asn Val Ser Arg Ser Thr Thr Glu Asp Phe Pro Leu Arg Leu Leu
65                  70                  75                  80

Ser Ala Ala Pro Ser Gln Thr Ser Val Tyr Phe Cys Ala Ala Glu Pro
                85                  90                  95

Ser Ala Glu Gly Lys Val Tyr Phe Gly Pro Gly Thr Arg Leu Thr Val
            100                 105                 110

Thr Glu Asp Leu Lys Asn Val Phe Pro Pro Glu Val Ala Val Phe Glu
        115                 120                 125

Pro Ser Glu Ala Glu Ile Ser His Thr Gln Lys Ala Thr Leu Val Cys
130                 135                 140

Leu Ala Thr Gly Phe Tyr Pro Asp His Val Glu Leu Ser Trp Trp Val
145                 150                 155                 160

Asn Gly Lys Glu Val His Ser Gly Val Cys Thr Asp Pro Gln Pro Leu
                165                 170                 175

Lys Glu Gln Pro Ala Leu Asn Asp Ser Arg Tyr Ala Leu Ser Ser Arg
            180                 185                 190

Leu Arg Val Ser Ala Thr Phe Trp Gln Asp Pro Arg Asn His Phe Arg
        195                 200                 205

Cys Gln Val Gln Phe Tyr Gly Leu Ser Glu Asn Asp Glu Trp Thr Gln
210                 215                 220

Asp Arg Ala Lys Pro Val Thr Gln Ile Val Ser Ala Glu Ala Trp Gly
225                 230                 235                 240

Arg Ala Asp

<210> SEQ ID NO 17
<211> LENGTH: 3111
<212> TYPE: DNA
<213> ORGANISM: Artificial Sequence
<220> FEATURE:
<223> OTHER INFORMATION: pGMT7 vector

<400> SEQUENCE: 17
```

```
gatctcgatc ccgcgaaatt aatacgactc actataggga gaccacaacg gtttccctct    60
agaaataatt ttgtttaact ttaagaagga gatatacata tgggatccat ggtaagcttg   120
aattccgatc cggctgctaa caaagcccga aaggaagctg agttggctgc tgccaccgct   180
gagcaataac tagcataacc ccttggggcc tctaaacggg tcttgagggg ttttttgctg   240
aaaggaggaa ctatatccgg ataattcttg aagacgaaag ggcctcgtga tacgcctatt   300
tttataggtt aatgtcatga taataatggt ttcttagacg tcaggtggca cttttcgggg   360
aaatgtgcgc ggaaccccta tttgtttatt tttctaaata cattcaaata tgtatccgct   420
catgagacaa taaccctgat aaatgcttca ataatatttt gttaaaattc gcgttaaatt   480
tttgttaaat cagctcattt tttaaccaat aggccgaaat cggcaaaatc ccttataaat   540
caaaagaata gaccgagata gggttgagtg ttgttccagt ttggaacaag agtccactat   600
taaagaacgt ggactccaac gtcaaagggc gaaaaaccgt ctatcagggc gatggcccac   660
tacgtgaacc atcaccctaa tcaagttttt tggggtcgag gtgccgtaaa gcactaaatc   720
ggaaccctaa agggagcccc cgatttagag cttgacgggg aaagccggcg aacgtggcga   780
gaaaggaagg gaagaaagcg aaaggagcgg gcgctagggc gctggcaagt gtagcggtca   840
cgctgcgcgt aaccaccaca cccgccgcgc ttaatgcgcc gctacagggc gcgtcaggtg   900
gcacttttcg gggaaatgtg cgcggaaccc ctatttgttt attttttctaa atacattcaa   960 atatgtatcc gctcatgaga caataaccct gataaatgct tcaataatat tgaaaagga  1020 agagtatgag tattcaacat ttccgtgtcg cccttattcc cttttttgcg gcattttgcc  1080
ttcctgtttt tgctcaccca gaaacgctgg tgaaagtaaa agatgctgaa gatcagttgg  1140
gtgcacgagt gggttacatc gaactggatc tcaacagcgg taagatcctt gagagttttc  1200
gccccgaaga acgttttcca atgatgagca cttttaaagt tctgctatgt ggcgcggtat  1260
tatcccgtgt tgacgccggg caagagcaac tcggtcgccg catacactat tctcagaatg  1320
acttggttga gtactcacca gtcacagaaa agcatcttac ggatggcatg acagtaagag  1380
aattatgcag tgctgccata accatgagtg ataacactgc ggccaactta cttctgacaa  1440
cgatcggagg accgaaggag ctaaccgctt ttttgcacaa catgggggat catgtaactc  1500
gccttgatcg ttgggaaccg gagctgaatg aagccatacc aaacgacgag cgtgacacca  1560
cgatgcctgc agcaatggca acaacgttgc gcaaactatt aactggcgaa ctacttactc  1620
tagcttcccg gcaacaatta atagactgga tggaggcgga taaagttgca ggaccacttc  1680
tgcgctcggc ccttccggct ggctggttta ttgctgataa atctggagcc ggtgagcgtg  1740
ggtctcgcgg tatcattgca gcactggggc cagatggtaa gccctcccgt atcgtagtta  1800
tctacacgac ggggagtcag gcaactatgg atgaacgaaa tagacagatc gctgagatag  1860
gtgcctcact gattaagcat tggtaactgt cagaccaagt ttactcatat atactttaga  1920
ttgatttaaa acttcatttt taatttaaaa ggatctaggt gaagatcctt ttgataatc  1980 tcatgaccaa aatcccttaa cgtgagtttt cgttccactg agcgtcagac cccgtagaaa  2040
agatcaaagg atcttcttga gatccttttt ttctgcgcgt aatctgctgc ttgcaaacaa  2100
aaaaaccacc gctaccagcg gtggtttgtt tgccggatca agagctacca actctttttc  2160
cgaaggtaac tggcttcagc agagcgcaga taccaaatac tgtccttcta gtgtagccgt  2220
agttaggcca ccacttcaag aactctgtag caccgcctac atacctcgct ctgctaatcc  2280
tgttaccagt ggctgctgcc agtggcgata agtcgtgtct taccgggttg gactcaagac  2340
gatagttacc ggataaggcg cagcggtcgg gctgaacggg gggttcgtgc acacagccca  2400
```

```
gcttggagcg aacgacctac accgaactga gatacctaca gcgtgagcta tgagaaagcg    2460
ccacgcttcc cgaagggaga aaggcggaca ggtatccggt aagcggcagg gtcggaacag    2520
gagagcgcac gagggagctt ccaggggaa acgcctggta tctttatagt cctgtcgggt    2580
ttcgccacct ctgacttgag cgtcgatttt tgtgatgctc gtcagggggg cggagcctat    2640
ggaaaaacgc cagcaacgcg gccttttttac ggttcctggc cttttgctgg ccttttgctc    2700
acatgttctt tcctgcgtta tcccctgatt ctgtggataa ccgtattacc gcctttgagt    2760
gagctgatac cgctcgccgc agccgaacga ccgagcgcag cgagtcagtg agcgaggaag    2820
cggaagagcg cctgatgcgg tattttctcc ttacgcatct gtgcggtatt tcacaccgca    2880
atggtgcact ctcagtacaa tctgctctga tgccgcatag ttaagccagt atacactccg    2940
ctatcgctac gtgactgggt catggctgcg ccccgacacc cgccaacacc cgctgacgcg    3000
ccctgacggg cttgtctgct cccggcatcc gcttacagac aagctgtgac cgtctccggg    3060
agctgcatgt gtcagaggtt ttcaccgtca tcaccgaaac gcgcgaggca g              3111
```

<210> SEQ ID NO 18
<211> LENGTH: 378
<212> TYPE: PRT
<213> ORGANISM: Artificial Sequence
<220> FEATURE:
<223> OTHER INFORMATION: A truncated recombinant VYG TCR beta chain
      including an introduced cysteine residue fused to wil-type
      human IL-2

<400> SEQUENCE: 18

```
Met Asn Ala Gly Val Thr Gln Thr Pro Lys Phe Gln Val Leu Lys Thr
 1               5                  10                  15

Gly Gln Ser Met Thr Leu Gln Cys Ala Gln Asp Met Asn His Glu Tyr
            20                  25                  30

Met Ser Trp Tyr Arg Gln Asp Pro Gly Met Gly Leu Arg Leu Ile His
        35                  40                  45

Tyr Ser Val Gly Ala Gly Ile Thr Asp Gln Gly Glu Val Pro Asn Gly
    50                  55                  60

Tyr Asn Val Ser Arg Ser Thr Thr Glu Asp Phe Pro Leu Arg Leu Leu
65                  70                  75                  80

Ser Ala Ala Pro Ser Gln Thr Ser Val Tyr Phe Cys Ala Ala Glu Pro
                85                  90                  95

Ser Ala Glu Gly Lys Val Tyr Phe Gly Pro Gly Thr Arg Leu Thr Val
            100                 105                 110

Thr Glu Asp Leu Lys Asn Val Phe Pro Pro Glu Val Ala Val Phe Glu
        115                 120                 125

Pro Ser Glu Ala Glu Ile Ser His Thr Gln Lys Ala Thr Leu Val Cys
    130                 135                 140

Leu Ala Thr Gly Phe Tyr Pro Asp His Val Glu Leu Ser Trp Trp Val
145                 150                 155                 160

Asn Gly Lys Glu Val His Ser Gly Val Cys Thr Asp Pro Gln Pro Leu
                165                 170                 175

Lys Glu Gln Pro Ala Leu Asn Asp Ser Arg Tyr Ala Leu Ser Ser Arg
            180                 185                 190

Leu Arg Val Ser Ala Thr Phe Trp Gln Asp Pro Arg Asn His Phe Arg
        195                 200                 205

Cys Gln Val Gln Phe Tyr Gly Leu Ser Glu Asn Asp Glu Trp Thr Gln
    210                 215                 220

Asp Arg Ala Lys Pro Val Thr Gln Ile Val Ser Ala Glu Ala Trp Gly
225                 230                 235                 240
```

```
Arg Ala Asp Pro Gly Ala Pro Thr Ser Ser Thr Lys Lys Thr Gln
            245                 250                 255

Leu Gln Leu Glu His Leu Leu Leu Asp Leu Gln Met Ile Leu Asn Gly
        260                 265                 270

Ile Asn Asn Tyr Lys Asn Pro Lys Leu Thr Arg Met Leu Thr Phe Lys
            275                 280                 285

Phe Tyr Met Pro Lys Lys Ala Thr Glu Leu Lys His Leu Gln Cys Leu
        290                 295                 300

Glu Glu Glu Leu Lys Pro Leu Glu Glu Val Leu Asn Leu Ala Gln Ser
305                 310                 315                 320

Lys Asn Phe His Leu Arg Pro Arg Asp Leu Ile Ser Asn Ile Asn Val
                325                 330                 335

Ile Val Leu Glu Leu Lys Gly Ser Glu Thr Thr Phe Met Cys Glu Tyr
            340                 345                 350

Ala Asp Glu Thr Ala Thr Ile Val Glu Phe Leu Asn Arg Trp Ile Thr
        355                 360                 365

Phe Cys Gln Ser Ile Ile Ser Thr Leu Thr
        370                 375

<210> SEQ ID NO 19
<211> LENGTH: 111
<212> TYPE: PRT
<213> ORGANISM: Artificial Sequence
<220> FEATURE:
<223> OTHER INFORMATION: A recombinant c8 VYG TCR alpha chain
      variable region

<400> SEQUENCE: 19

Met Gln Lys Glu Val Glu Gln Asn Ser Gly Pro Leu Ser Val Pro Glu
1               5                   10                  15

Gly Ala Ile Ala Ser Leu Asn Cys Thr Tyr Ser Asp Arg Gly Ser Gln
            20                  25                  30

Ser Phe Phe Trp Tyr Arg Gln Tyr Ser Gly Lys Ser Pro Glu Leu Ile
        35                  40                  45

Met Ser Ile Tyr Ser Asn Gly Asp Lys Glu Asp Gly Arg Phe Thr Ala
    50                  55                  60

Gln Leu Asn Lys Ala Ser Gln Tyr Val Ser Leu Leu Thr Arg Asp Ser
65                  70                  75                  80

Gln Pro Ser Asp Ser Ala Thr Tyr Leu Cys Ala Gln Ser Gln Cys Thr
                85                  90                  95

Glu Asn Gln Phe Gly Ala Gly Thr Gln Val Val Val Thr Pro Asp
            100                 105                 110

<210> SEQ ID NO 20
<211> LENGTH: 204
<212> TYPE: PRT
<213> ORGANISM: Artificial Sequence
<220> FEATURE:
<223> OTHER INFORMATION: A recombinant truncated soluble c8 VYG TCR
      alpha chain including an introduced cysteine residue

<400> SEQUENCE: 20

Met Gln Lys Glu Val Glu Gln Asn Ser Gly Pro Leu Ser Val Pro Glu
1               5                   10                  15

Gly Ala Ile Ala Ser Leu Asn Cys Thr Tyr Ser Asp Arg Gly Ser Gln
            20                  25                  30

Ser Phe Phe Trp Tyr Arg Gln Tyr Ser Gly Lys Ser Pro Glu Leu Ile
        35                  40                  45
```

```
Met Ser Ile Tyr Ser Asn Gly Asp Lys Glu Asp Gly Arg Phe Thr Ala
        50                  55                  60

Gln Leu Asn Lys Ala Ser Gln Tyr Val Ser Leu Leu Thr Arg Asp Ser
 65                  70                  75                  80

Gln Pro Ser Asp Ser Ala Thr Tyr Leu Cys Ala Gln Ser Gln Cys Thr
                85                  90                  95

Glu Asn Gln Phe Gly Ala Gly Thr Gln Val Val Val Thr Pro Asp Ile
            100                 105                 110

Gln Asn Pro Asp Pro Ala Val Tyr Gln Leu Arg Asp Ser Lys Ser Ser
        115                 120                 125

Asp Lys Ser Val Cys Leu Phe Thr Asp Phe Asp Ser Gln Thr Asn Val
    130                 135                 140

Ser Gln Ser Lys Asp Ser Asp Val Tyr Ile Thr Asp Lys Cys Val Leu
145                 150                 155                 160

Asp Met Arg Ser Met Asp Phe Lys Ser Asn Ser Ala Val Ala Trp Ser
                165                 170                 175

Asn Lys Ser Asp Phe Ala Cys Ala Asn Ala Phe Asn Asn Ser Ile Ile
            180                 185                 190

Pro Glu Asp Thr Phe Phe Pro Ser Pro Glu Ser Ser
        195                 200

<210> SEQ ID NO 21
<211> LENGTH: 9
<212> TYPE: PRT
<213> ORGANISM: Homo sapiens

<400> SEQUENCE: 21

Ile Leu Ala Lys Phe Leu His Trp Leu
 1               5

<210> SEQ ID NO 22
<211> LENGTH: 9
<212> TYPE: PRT
<213> ORGANISM: Homo sapiens

<400> SEQUENCE: 22

Leu Leu Phe Gly Tyr Pro Val Tyr Val
 1               5
```

T CELL RECEPTORS WHICH SPECIFICALLY BIND TO VYGFVRACL-HLA-A24

This application is a national phase application of PCT/GB2006/001857 filed May 19, 2006, which was published in English under PCT Article 21(2) on Nov. 30, 2006 and which claims the benefit of PCT/GB2005/002078 filed May 25, 2005 and GB 0524477.7 filed Nov. 30, 2005.

The present invention relates to isolated T cell receptors (TCRs) having the property of specifically binding to VYGFVRACL (SEQ ID NO:1)-HLA-A24.

This application incorporates by reference a 28 kb text file created on Feb. 7, 2011 and named "SN11151190_sequencelisting.txt," which is the sequence listing for this application.

BACKGROUND TO THE INVENTION

The VYGFVRACL (SEQ ID NO:1) peptide is derived from the catalytic sub-unit of the Telomerase protein. (See Meyerson et al., (1997) Cell 90: 785-795 and Nakamura et al., (1997) Science 277: 955-9) These studies describe the near-simultaneous discovery of the DNA and deduced amino acid sequence of the Telomerase catalytic subunit from database sequences. Both studies note that Telomerase catalytic sub-unit activity is associated with human cancer. The Class I HLA molecules of these cancerous cells present peptides from this protein, including VYGFVRACL (SEQ ID NO:1). This peptide is presented in the context of HLA-A24 (Arai et al., (2001) Blood 97 (9): 2903-2907, and Tajima et al., Int. J. Cancer (2004) 110: 403-412). Therefore, the VYGFVRACL (SEQ ID NO:1)-HLA-A24 complex provides a cancer marker that the TCRs of the invention can target, for example for the purpose of delivering cytotoxic agents to the cancer cells.

BRIEF DESCRIPTION OF THE INVENTION

This invention makes available for the first time isolated T cell receptors (TCRs) having the property of specifically binding to VYGFVRACL (SEQ ID NO:1)-HLA-A24. Such TCRs are useful, either alone or associated with a therapeutic agent for targeting cancer cells presenting that complex.

DETAILED DESCRIPTION OF THE INVENTION

The present invention provides isolated TCRs having the property of specifically binding to VYGFVRACL (SEQ ID NO:1)-HLA-A24. Preferably, the VYGFVRACL (SEQ ID NO: 1) peptide is presented in the context of HLA-A*2402.

The TCRs of the having the property of specifically binding to VYGFVRACL (SEQ ID NO:1)-HLA-A24, are referred to herein as VYG-A24 TCRs. "Parental" VYG-A24 TCRs are defined as those which comprise the alpha chain variable region shown in FIG. 1a (SEQ ID NO: 2) and the beta chain variable region shown in FIG. 1b (SEQ ID NO: 3). For example, a disulfide-linked soluble version of the parental VYG-A24 TCR consists of the TCR alpha chain shown in FIG. 5a (SEQ ID NO: 15) and the TCR beta chain shown in FIG. 5b (SEQ ID NO: 16).

One embodiment of the invention is provided by non-natural TCRs having the property of specifically binding to VYGFVRACL (SEQ ID NO: 1)-HLA-A24. That is such TCRs of the invention consist of sequences not found in nature.

Another embodiment provides a TCR of the invention CHARACTERISED IN THAT said TCR has a $K_D$ for the said VYGFVRACL (SEQ ID NO: 1)-HLA-A*02402 complex of 5 µM or less. Example 4 herein provides details of a Biacore-based method suitable for determining the $K_D$ for the interaction between soluble TCRs and pMHC molecules.

A further aspect is provided by an isolated TCR of the invention comprising the Complimentarity Determining Regions (CDRs) present in FIG. 10b (SEQ ID NO 20) and/or FIG. 3b (SEQ ID No: 12). The CDRs of these TCR chains are underlined in the corresponding figures.

The parental VYG-A24 TCR specific for VYGFVRACL (SEQ ID NO: 1)-HLA-A24 complex has the following Vα chain and Vβ chain gene usage:
Alpha chain—TRAV22
Beta chain:—TRBV 6.5

VYG-A24 TCRs can be used as a template from which other TCRs of the invention can be produced. Thus the invention includes in one embodiment TCRs which are mutated relative to the parental VYG-A24 TCR α chain variable region (see FIG. 1a and SEQ ID No: 2) and/or β chain variable region (see FIG. 1b and SEQ ID NO: 3) in at least one complementarity determining region (CDR) and/or variable domain framework region thereof. In a related embodiment the invention also encompasses TCRs which are mutated relative to the VYG-A24 TCR α chain variable region (see FIG. 10a and SEQ ID No: 19) and in at least one complementarity determining region (CDR) and/or variable domain framework region thereof.

It is also contemplated that other hypervariable regions in the variable domains of the TCRs of the invention, such as the hypervariable 4 (HV4) regions, may be mutated to produce a high affinity mutant TCR which retains the property of specifically binding to VYGFVRACL (SEQ ID NO:1)-HLA-A24.

Phage display provides one means by which libraries of TCR variants can be generated. Methods suitable for the phage display and subsequent screening of libraries of TCR variants each containing a non-native disulfide interchain bond are detailed in (Li et al., (2005) Nature Biotech 23 (3): 349-354) and WO 2004/04404.

Native TCRs exist in heterodimeric αβ or γδ forms. However, recombinant TCRs consisting of a single TCR α or TCR β chain have previously been shown to bind to peptide MHC molecules. Furthermore, recombinant TCRs consisting of αα or ββ homodimers have previously been shown to bind to peptide MHC molecules. Therefore, other embodiments of the invention are provided by TCR αα or TCR ββ homodimers.

In one embodiment TCRs of the invention comprise both an α chain variable region and an TCR β chain variable region.

Unless stated to the contrary, the TCR amino acid sequences herein are generally provided including an N-terminal methionine (Met or M) residue. As will be known to those skilled in the art this residue may be removed during the production of recombinant proteins. As will also be obvious to those skilled in the art, it may be possible to truncate the sequences provided at the C-terminus and/or N-terminus thereof, by 1, 2, 3, 4, 5 or more residues, without substantially affecting the pMHC binding characteristics of the TCR, all such trivial variants are encompassed by the present invention.

As used herein the term "isolated TCRs" means TCRs in a format other than one found in nature, for example a soluble TCR or a TCR presented on a cell which was non-naturally transfected with the genetic material encoding said TCR.

As used herein the term "variable region" is understood to encompass all amino acids of a given TCR which are not included within the constant domain as encoded by the TRAC gene for TCR α chains and either the TRBC1 or TRBC2 for TCR β chains. (T cell receptor Factsbook, (2001) LeFranc and LeFranc, Academic Press, ISBN 0-12-441352-8).

Preferred embodiments provide a TCR of the invention comprising:
the α chain variable region shown in FIG. 1a (SEQ ID NO: 2) and the β chain variable region shown in FIG. 1b (SEQ ID NO: 3), or phenotypically silent variants thereof. For example, a TCR comprising the amino acid sequences of SEQ ID NO: 15 (FIG. 5a) and SEQ ID NO: 16 (FIG. 5b). This TCR α chain is that of a known TCR specific for the ILAK-FLHWL (SEQ ID NO:21)-HLA-A*0201 complex. The DNA and amino acid sequence of this TCR chain α was first published in WO 2005/116075.

Other preferred embodiments provide a TCR of the invention comprising:
the α chain variable region shown in FIG. 10a (SEQ ID NO: 19) and the β chain variable region shown in FIG. 1b (SEQ ID NO: 3), or phenotypically silent variants thereof. For example, a TCR comprising the amino acid sequences of SEQ ID NO: 20 (FIG. 10b) and SEQ ID NO: 16 (FIG. 5b).

In a related embodiment such TCRs of the invention may further comprise the truncated α chain constant region amino acid sequence shown in FIG. 6a (SEQ ID NO: 4) and one of the truncated β chain amino acid constant region sequences shown in FIGS. 6b and 6c (SEQ ID NOs: 5 and 6) or phenotypically silent variants thereof.

As used herein the term "phenotypically silent variants" is understood to refer to those TCRs which retain the property of binding to the Telomerase-derived VYGFVRACL (SEQ ID NO:1) peptide presented in the context of HLA-A24. For example, as is known to those skilled in the art, it may be possible to produce TCRs that incorporate minor changes in the constant domains and/or variable regions thereof compared to those detailed above without altering the affinity and/or off-rate for the interaction with the VYGFVRACL (SEQ ID NO:1)-HLA-A24 complex. Such trivial variants are included in the scope of this invention. Those TCRs in which one or more conservative substitutions have been made also form part of this invention.

In one broad aspect, the TCRs of the invention are in the form of either single chain TCRs (scTCRs) or dimeric TCRs (dTCRs), including but not limited to, those described in WO 04/033685 and WO 03/020763 respectively.

A suitable scTCR form comprises a first segment constituted by an amino acid sequence corresponding to a TCR α chain variable region, a second segment constituted by an amino acid sequence corresponding to a TCR β chain variable region sequence fused to the N terminus of an amino acid sequence corresponding to a TCR β chain constant domain extracellular sequence, and a linker sequence linking the C terminus of the first segment to the N terminus of the second segment.

Alternatively the first segment may be constituted by an amino acid sequence corresponding to a TCR β chain variable region; the second segment may be constituted by an amino acid sequence corresponding to a TCR α chain variable region sequence fused to the N terminus of an amino acid sequence corresponding to a TCR α chain constant domain extracellular sequence The above scTCRs may further comprise a disulfide bond between the first and second chains, said disulfide bond being one which has no equivalent in native αβ T cell receptors, and wherein the length of the linker sequence and the position of the disulfide bond being such that the variable region sequences of the first and second segments are mutually orientated substantially as in native αβ T cell receptors.

More specifically the first segment may be constituted by an amino acid sequence corresponding to a TCR α, chain variable region sequence fused to the N terminus of an amino acid sequence corresponding to a TCR α chain constant domain extracellular sequence, the second segment may be constituted by an amino acid sequence corresponding to a TCR β chain variable region fused to the N terminus of an amino acid sequence corresponding to TCR β chain constant domain extracellular sequence, and a disulfide bond may be provided between the first and second chains, said disulfide bond being one which has no equivalent in native αβ T cell receptors.

In the above scTCR forms, the linker sequence may link the C terminus of the first segment to the N terminus of the second segment, and may have the formula —PGGG-(SGGGG)$_n$-P— wherein n is 5 or 6 and P is proline, G is glycine and S is serine:

```
                                              (SEQ ID NO: 7)
-PGGG-SGGGGSGGGGSGGGGSGGGGSGGGG-P (SEQ ID NO: 8)
-PGGG-SGGGGSGGGGSGGGGSGGGGSGGGGSGGGG-P
```

A suitable dTCR form of the TCRs of the present invention comprises a first polypeptide wherein a sequence corresponding to a TCR α chain variable region sequence is fused to the N terminus of a sequence corresponding to a TCR α chain constant domain extracellular sequence, and a second polypeptide wherein a sequence corresponding to a TCR β chain variable region sequence fused to the N terminus a sequence corresponding to a TCR β chain constant domain extracellular sequence, the first and second polypeptides being linked by a disulfide bond which has no equivalent in native αβ T cell receptors.

The first polypeptide may comprise a TCR α chain variable region sequence is fused to the N terminus of a sequence corresponding to a TCR α chain constant domain extracellular sequence, and a second polypeptide wherein a sequence corresponding to a TCR β chain variable region sequence is fused to the N terminus a sequence corresponding to a TCR β chain constant domain extracellular sequence, the first and second polypeptides being linked by a disulfide bond between cysteine residues substituted for Thr 48 of exon 1 of TRAC*01 and Ser 57 of exon 1 of TRBC1*01 or TRBC2*01 or the non-human equivalent thereof ("TRAC" etc. nomenclature herein as per *T cell receptor Factsbook*, (2001) LeFranc and LeFranc, Academic Press, ISBN 0-12-441352-8)

The dTCR or scTCR form of the TCRs of the invention may have amino acid sequences corresponding to human αβ TCR extracellular constant and variable region sequences, and a disulfide bond may link amino acid residues of the said constant domain sequences, which disulfide bond has no equivalent in native TCRs. The disulfide bond is between cysteine residues corresponding to amino acid residues whose β carbon atoms are less than 0.6 nm apart in native TCRs, for example between cysteine residues substituted for Thr 48 of exon 1 of TRAC*01 and Ser 57 of exon 1 of TRBC1*01 or TRBC2*01 or the non-human equivalent thereof. Other sites where cysteines can be introduced to form the disulfide bond are the following residues in exon 1 of TRAC*01 for the TCR α chain and TRBC1*01 or TRBC2*01 for the TCR β chain:

| TCR α chain | TCR β chain | Native β carbon separation (nm) |
|---|---|---|
| Thr 45 | Ser 77 | 0.533 |
| Tyr 10 | Ser 17 | 0.359 |
| Thr 45 | Asp 59 | 0.560 |
| Ser 15 | Glu 15 | 0.59 |

In addition to the non-native disulfide bond referred to above, the dTCR or scTCR form of the TCRs of the invention may include a disulfide bond between residues corresponding to those linked by a disulfide bond in native TCRs.

The TCRs of the invention preferably do not contain a sequence corresponding to transmembrane sequence.

The TCRs of the invention preferably do not contain a sequence corresponding to cytoplasmic sequences of native TCRs.

The dTCR or scTCR form of the TCRs of the invention may comprise a first polypeptide wherein a sequence corresponding to a TCR α chain variable region sequence is fused to the N terminus of a sequence corresponding to a TCR α chain constant domain extracellular sequence, and a second polypeptide wherein a sequence corresponding to a TCR β chain variable region sequence fused to the N terminus a sequence corresponding to a TCR β chain constant domain extracellular sequence, the first and second polypeptides being linked by a disulfide between cysteine residues substituted for Thr 48 of exon 1 of TRAC*01 and Ser 57 of exon 1 of TRBC1*01 or TRBC2*01 or the non-human equivalent thereof.

One currently preferred embodiment of the invention provides a TCR comprising the α chain amino acid sequence of SEQ ID NO: 15 and β chain amino acid sequence SEQ ID NO: 16. Another currently preferred embodiment of the invention provides a TCR comprising the α chain amino acid sequence of SEQ ID NO: 20 and β chain amino acid sequence SEQ ID NO: 16.

Also provided is a nucleic acid or nucleic acids encoding TCRs of the invention. Such a nucleic acid or nucleic acids may be provided in a form which has been adapted for expression in a prokaryote or eukaryote host cell. Suitable host cells include, but are not limited to, bacterial, yeast, mammalian or insect cells. For example, the host cell may be a human T cell or a human haematopoietic stem cell.

Such adapted nucleic acid or nucleic acids is/are mutated to reflect the codon preference of the host cell in to which it is introduced. The mutations introduced are silent mutations which do not affect the amino acid sequence of the polypeptide or polypeptides thereby encoded. GeneArt (Regensburg, Germany) offer a suitable nucleic acid optimisation service (GeneOptimizer™) WO 2004/059556, owned by GeneArt, provides further details of the optimisation process.

Other currently preferred embodiments of the invention are provided by nucleic acids consisting of a full-length TCR α chain DNA sequence and a full-length TCR β chain DNA sequence. A nucleic acid complementary to any of the foregoing, or a corresponding RNA sequence also forms part of this invention. Furthermore, as will be obvious to those skilled in the art such nucleic acid or nucleic acids encoding TCRs of the invention may also comprise non-coding (intron) sequences.

As will be obvious to those skilled in the art such full-length TCR chain DNA sequences encode for the following sequences:
A leader sequence and the extracellular, transmembrane, and cytoplasmic TCR sequences.

PEGylated TCR Monomers

In one particular embodiment a TCR of the invention is associated with at least one polyalkylene glycol chain. This association may be caused in a number of ways known to those skilled in the art. In a preferred embodiment the polyalkylene chain(s) is/are covalently linked to the TCR. In a further embodiment the polyethylene glycol chains of the present aspect of the invention comprise at least two polyethylene repeating units.

Multivalent TCR Complexes

One aspect of the invention provides a multivalent TCR complex comprising at least two TCRs of the invention. In one embodiment of this aspect, at least two TCR molecules are linked via linker moieties to form multivalent complexes. Preferably the complexes are water soluble, so the linker moiety should be selected accordingly. Furthermore, it is preferable that the linker moiety should be capable of attachment to defined positions on the TCR molecules, so that the structural diversity of the complexes formed is minimised. One embodiment of the present aspect is provided by a TCR complex of the invention wherein the polymer chain or peptidic linker sequence extends between amino acid residues of each TCR which are not located in a variable region sequence of the TCR.

Since the complexes of the invention may be for use in medicine, the linker moieties should be chosen with due regard to their pharmaceutical suitability, for example their immunogenicity.

Examples of linker moieties which fulfill the above desirable criteria are known in the art, for example the art of linking antibody fragments.

There are two classes of linker that are preferred for use in the production of multivalent TCR molecules of the present invention. These are non-peptidic polymer chains or peptidic linker sequences. A TCR complex of the invention in which the TCRs are linked by a polyalkylene glycol chain provides one embodiment of the present aspect.

The first are hydrophilic polymers such as polyalkylene glycols. The most commonly used of this class are based on polyethylene glycol or PEG, the structure of which is shown below.

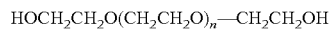

Wherein n is greater than two. However, others are based on other suitable, optionally substituted, polyalkylene glycols include polypropylene glycol, and copolymers of ethylene glycol and propylene glycol.

Such polymers may be used to treat or conjugate therapeutic agents, particularly polypeptide or protein therapeutics, to achieve beneficial changes to the PK profile of the therapeutic, for example reduced renal clearance, improved plasma half-life, reduced immunogenicity, and improved solubility. Such improvements in the PK profile of the PEG-therapeutic conjugate are believe to result from the PEG molecule or molecules forming a 'shell' around the therapeutic which sterically hinders the reaction with the immune system and reduces proteolytic degradation. (Casey et al, (2000) *Tumor Targetting* 4: 235-244) The size of the hydrophilic polymer used my in particular be selected on the basis of the intended therapeutic use of the TCR complex. Thus for example, where the product is intended to leave the circulation and penetrate tissue, for example for use in the treatment of a tumour, it may be advantageous to use low molecular weight polymers in the order of 5 KDa. There are numerous review papers and books that detail the use of PEG and similar molecules in pharmaceutical formulations. For example, see Harris (1992) *Polyethylene Glycol Chemistry—Biotechnical and Biomedical*

*Applications*, Plenum, New York, N.Y. or Harris & Zalipsky (1997) *Chemistry and Biological Applications of Polyethylene Glycol* ACS Books, Washington, D.C.

The polymer used can have a linear or branched conformation. Branched PEG molecules, or derivatives thereof, can be induced by the addition of branching moieties including glycerol and glycerol oligomers, pentaerythritol, sorbitol and lysine.

Usually, the polymer will have a chemically reactive group or groups in its structure, for example at one or both termini, and/or on branches from the backbone, to enable the polymer to link to target sites in the TCR. This chemically reactive group or groups may be attached directly to the hydrophilic polymer, or there may be a spacer group/moiety between the hydrophilic polymer and the reactive chemistry as shown below:

Reactive chemistry-Hydrophilic polymer-Reactive chemistry

Reactive chemistry-Spacer-Hydrophilic polymer-Spacer-Reactive chemistry

The spacer used in the formation of constructs of the type outlined above may be any organic moiety that is a non-reactive, chemically stable, chain, Such spacers include, by are not limited to the following:

—$(CH_2)_n$— wherein n=2 to 5

—$(CH_2)_3NHCO(CH_2)_2$

A TCR complex of the invention in which a divalent alkylene spacer radical is located between the polyalkylene glycol chain and its point of attachment to a TCR of the complex provides a further embodiment of the present aspect.

A TCR complex of the invention in which the polyalkylene glycol chain comprises at least two polyethylene glycol repeating units provides a further embodiment of the present aspect.

There are a number of commercial suppliers of hydrophilic polymers linked, directly or via a spacer, to reactive chemistries that may be of use in the present invention. These suppliers include Nektar Therapeutics (CA, USA), NOF Corporation (Japan), Sunbio (South Korea) and Enzon Pharmaceuticals (NJ, USA).

Commercially available hydrophilic polymers linked, directly or via a spacer, to reactive chemistries that may be of use in the present invention include, but are not limited to, the following:

| PEG linker Description | Source of PEG | Catalogue Number |
|---|---|---|
| TCR Monomer attachment | | |
| 5K linear (Maleimide) | Nektar | 2D2MOHO1 |
| 20K linear (Maleimide) | Nektar | 2D2MOPO1 |
| 20K linear (Maleimide) | NOF Corporation | SUNBRIGHT ME-200MA |
| 20K branched (Maleimide) | NOF Corporation | SUNBRIGHT GL2-200MA |
| 30K linear (Maleimide) | NOF Corporation | SUNBRIGHT ME-300MA |
| 40K branched PEG (Maleimide) | Nektar | 2D3XOTO1 |
| 5K-NP linear (for Lys attachment) | NOF Corporation | SUNBRIGHT MENP-50H |
| 10K-NP linear (for Lys attachment) | NOF Corporation | SUNBRIGHT MENP-10T |
| 20K-NP linear (for Lys attachment) | NOF Corporation | SUNBRIGHT MENP-20T |

-continued

| PEG linker Description | Source of PEG | Catalogue Number |
|---|---|---|
| TCR dimer linkers | | |
| 3.4K linear (Maleimide) | Nektar | 2D2DOFO2 |
| 5K forked (Maleimide) | Nektar | 2D2DOHOF |
| 10K linear (with orthopyridyl ds-linkers in place of Maleimide) | Sunbio | |
| 20K forked (Maleimide) | Nektar | 2D2DOPOF |
| 20K linear (Maleimide) | NOF Corporation | |
| 40K forked (Maleimide) | Nektar | 2D3XOTOF |
| Higher order TCR multimers | | |
| 15K, 3 arms, Mal$_3$ (for trimer) | Nektar | OJOONO3 |
| 20K, 4 arms, Mal$_4$(for tetramer) | Nektar | OJOOPO4 |
| 40K, 8 arms, Mal$_8$(for octamer) | Nektar | OJOOTO8 |

A wide variety of coupling chemistries can be used to couple polymer molecules to protein and peptide therapeutics. The choice of the most appropriate coupling chemistry is largely dependant on the desired coupling site. For example, the following coupling chemistries have been used attached to one or more of the termini of PEG molecules (Source: Nektar Molecular Engineering Catalogue 2003):

N-maleimide
    Vinyl sulfone
    Benzotriazole carbonate
    Succinimidyl proprionate
    Succinimidyl butanoate
    Thio-ester
    Acetaldehydes
    Acrylates
    Biotin
    Primary amines As stated above non-PEG based polymers also provide suitable linkers for multimerising the TCRs of the present invention. For example, moieties containing maleimide termini linked by aliphatic chains such as BMH and BMOE (Pierce, products Nos. 22330 and 22323) can be used.

Peptidic linkers are the other class of TCR linkers. These linkers are comprised of chains of amino acids, and function to produce simple linkers or multimerisation domains onto which TCR molecules can be attached. The biotin/streptavidin system has previously been used to produce TCR tetramers (see WO/99/60119) for in-vitro binding studies. However, strepavidin is a microbially-derived polypeptide and as such not ideally suited to use in a therapeutic.

A TCR complex of the invention in which the TCRs are linked by a peptidic linker derived from a human multimerisation domain provides a further embodiment of the present aspect.

There are a number of human proteins that contain a multimerisation domain that could be used in the production of multivalent TCR complexes. For example the tetramerisation domain of p53 which has been utilised to produce tetramers of scFv antibody fragments which exhibited increased serum persistence and significantly reduced off-rate compared to the monomeric scFv fragment. (Willuda et al. (2001) *J. Biol. Chem.* 276 (17): 14385-14392) Haemoglobin also has a tetramerisation domain that could potentially be used for this kind of application.

A multivalent TCR complex of the invention comprising at least two TCRs provides a final embodiment of this aspect, wherein at least one of said TCRs is associated with a therapeutic agent.

In one aspect a TCR (or multivalent complex thereof) of the present invention may alternatively or additionally comprise a reactive cysteine at the C-terminal or N-terminal of the α or β chains thereof.

Diagnostic and Therapeutic Use

In one aspect the TCR of the invention may be associated with a therapeutic agent or detectable moiety. For example, said therapeutic agent or detectable moiety may be covalently linked to the TCR.

In one embodiment of the invention said therapeutic agent or detectable moiety is covalently linked to the C-terminus of one or both TCR chains.

In one aspect the scTCR or one or both of the dTCR chains of TCRs of the present invention may be labelled with an detectable moiety, for example a label that is suitable for diagnostic purposes. Such labelled TCRs are useful in a method for detecting a VYGFVRACL (SEQ ID NO:1)-HLA-A*0201 complex which method comprises contacting the TCR ligand with a TCR (or a multimeric high avidity TCR complex) which is specific for the TCR ligand; and detecting binding to the TCR ligand. In tetrameric TCR complexes formed for example, using biotinylated heterodimers, fluorescent streptavidin can be used to provide a detectable label. Such a fluorescently-labelled TCR tetramer is suitable for use in FACS analysis, for example to detect antigen presenting cells carrying the VYGFVRACL (SEQ ID NO:1)-HLA-A*0201 complex for which these TCRs are specific.

Another manner in which the soluble TCRs of the present invention may be detected is by the use of T cell specific antibodies (e.g. anti-CD3 antibodies), in particular monoclonal antibodies. There are many commercially available anti-T cell antibodies, such as αF1 and βF1, which recognise the constant domains of TCR α and β chains, respectively.

In a further aspect a TCR (or multivalent complex thereof) of the present invention may alternatively or additionally be associated with (e.g. covalently or otherwise linked to) a therapeutic agent which may be, for example, a cytotoxic moiety for use in cell killing, or an immune effector molecule such as an interleukin or a cytokine. A multivalent TCR complex of the invention may have enhanced binding capability for a TCR ligand compared to a non-multimeric wild-type or T cell receptor heterodimer of the invention. Thus, the multivalent TCR complexes according to the invention are particularly useful for tracking or targeting cells presenting particular antigens in vitro or in vivo, and are also useful as intermediates for the production of further multivalent TCR complexes having such uses. These TCRs or multivalent TCR complexes may therefore be provided in a pharmaceutically acceptable formulation for use in vivo.

The invention also provides a method for delivering a therapeutic agent to a target cell, which method comprises contacting potential target cells with a TCR or multivalent TCR complex in accordance with the invention under conditions to allow attachment of the TCR or multivalent TCR complex to the target cell, said TCR or multivalent TCR complex being specific for the VYGFVRACL (SEQ ID NO:1)-HLA-A24 complex and having the therapeutic agent associated therewith.

In particular, the soluble TCR or multivalent TCR complex of the present invention can be used to deliver therapeutic agents to the location of cells presenting a particular antigen. This would be useful in many situations and, in particular, against tumours. A therapeutic agent could be delivered such that it would exercise its effect locally but not only on the cell it binds to. Thus, one particular strategy envisages anti-tumour molecules linked to TCRs or multivalent TCR complexes according to the invention specific for tumour antigens.

Many therapeutic agents could be employed for this use, for instance radioactive compounds, enzymes (perforin for example) or chemotherapeutic agents (cis-platin for example). To ensure that toxic effects are exercised in the desired location the toxin could be inside a liposome linked to streptavidin so that the compound is released slowly. This will prevent damaging effects during the transport in the body and ensure that the toxin has maximum effect after binding of the TCR to the relevant antigen presenting cells.

Other suitable therapeutic agents include:

small molecule cytotoxic agents, i.e. compounds with the ability to kill mammalian cells having a molecular weight of less than 700 daltons. Such compounds could also contain toxic metals capable of having a cytotoxic effect. Furthermore, it is to be understood that these small molecule cytotoxic agents also include pro-drugs, i.e. compounds that decay or are converted under physiological conditions to release cytotoxic agents. Examples of such agents include cis-platin, maytansine derivatives, rachelmycin, calicheamicin, docetaxel, etoposide, gemcitabine, ifosfamide, irinotecan, melphalan, mitoxantrone, sorfimer sodiumphotofrin II, temozolmide, topotecan, trimetreate glucuronate, auristatin E vincristine and doxorubicin;

peptide cytotoxins, i.e. proteins or fragments thereof with the ability to kill mammalian cells. Including but not limited to, ricin, diphtheria toxin, pseudomonas bacterial exotoxin A and variants thereof such a PE38, DNAase and RNAase;

radio-nuclides, i.e. unstable isotopes of elements which decay with the concurrent emission of one or more of α or β particles, or γ rays. including but not limited to, iodine 131, rhenium 186, indium 111, yttrium 90, bismuth 210 and 213, actinium 225 and astatine 213; chelating agents may be used to facilitate the association of these radio-nuclides to the TCRs, or multimers thereof;

prodrugs, including but not limited to, antibody directed enzyme pro-drugs;

immuno-stimulants, i.e. moieties which stimulate immune response. Including but not limited to, cytokines such as IL-2 and IFN, superantigens and mutants thereof, pHLA complexes and chemokines such as IL-8, platelet factor 4, melanoma growth stimulatory protein, etc, antibodies or fragments thereof, complement activators, xenogeneic protein domains, allogeneic protein domains, viral/bacterial protein domains, viral/bacterial peptides and anti-T cell determinant antibodies (e.g. anti-CD3 or anti-CD28).

Functional Antibody Fragments and Variants

Antibody fragments and variants/analogues which are suitable for use in the compositions and methods described herein include, but are not limited to, the following.

Antibody Fragments

As is known to those skilled in the art, it is possible to produce fragments of a given antibody which retain substantially the same binding characteristics as those of the parent antibody. The following provides details of such fragments:

Minibodies—These constructs consist of antibodies with a truncated Fc portion. As such they retain the complete binding domains of the antibody from which are derived.

Fab fragments—These comprise a single immunoglobulin light chain covalently-linked to part of an immunoglobulin heavy chain. As such, Fab fragments comprise a single antigen combining site. Fab fragments are defined by the portion of an IgG that can be liberated by treatment with papain. Such fragments are commonly produced via recombinant DNA techniques. (Reeves et al., (2000) Lecture Notes on Immunology (4th Edition) Published by Blackwell Science)

F(ab')$_2$ fragments—These comprise both antigen combining sites and the hinge region from a single antibody. F(ab')$_2$ fragments are defined by the portion of an IgG that can be liberated by treatment with pepsin. Such fragments are commonly produced via recombinant DNA techniques. (Reeves et al., (2000) Lecture Notes on Immunology (4th Edition) Published by Blackwell Science)

Fv fragments—These comprise an immunoglobulin variable heavy domain linked to an immunoglobulin variable light domain. A number of Fv designs have been produced. These include dsFvs, in which the association between the two domains is enhanced by an introduced disulfide bond. Alternatively, scFvs can be formed using a peptide linker to bind the two domains together as a single polypeptide. Fvs constructs containing a variable region of a heavy or light immunoglobulin chain associated to the variable and constant domain of the corresponding immunoglobulin heavy or light chain have also been produced. FV have also been multimerised to form diabodies and triabodies (Maynard et al., (2000) *Annu Rev Biomed Eng* 2 339-376)

Nanobodies™—These constructs, marketed by Ablynx (Belgium), comprise synthetic single immunoglobulin variable heavy domain derived from a camelid (e.g. camel or llama) antibody.

Domain Antibodies—These constructs, marketed by Domantis (Belgium), comprise an affinity matured single immunoglobulin variable heavy domain or immunoglobulin variable light domain.

Antibody Variants and Analogues

The defining functional characteristic of antibodies in the context of the present invention is their ability to bind specifically to a target ligand. As is known to those skilled in the art it is possible to engineer such binding characteristics into a range of other proteins. Examples of antibody variants and analogues suitable for use in the compositions and methods of the present invention include, but are not limited to, the following.

Protein scaffold-based binding polypeptides—This family of binding constructs comprise mutated analogues of proteins which contain native binding loops. Examples include Affibodies, marketed by Affibody (Sweden), which are based on a three-helix motif derived from one of the IgG binding domains of *Staphylococcus aureus* Protein A. Another example is provided by Evibodies, marketed by EvoGenix (Australia) which are based on the extracellular domains of CTLA-4 into which domains similar to antibody binding loops are grafted. A final example, Cytokine Traps marketed by Regeneron Pharmaceuticals (US), graft cytokine receptor domains into antibody scaffolds. (Nygren et al., (2000) *Current Opinion in Structural biology* 7:463-469) provides a review of the uses of scaffolds for engineering novel binding sites in proteins. This review mentions the following proteins as sources of scaffolds: CP1 zinc finger, Tendamistat, Z domain (a protein A analogue), PST1, Coiled coils, LACI-D1 and cytochrome $b_{562}$. Other protein scaffold studies have reported the use of Fibronectin, Green fluorescent protein (GFP) and ankyrin repeats.

As is known to those skilled in the art antibodies or fragments, variants or analogues thereof can be produced which bind to various parts of a given protein ligand. For example, anti-CD3 antibodies can be raised to any of the polypeptide chains from which this complex is formed (i.e. γ, δ, ε, ζ, and η CD3 chains) Antibodies which bind to the .epsilon. CD3 chain are the preferred anti-CD3 antibodies for use in the compositions and methods of the present invention.

Soluble TCRs or multivalent TCR complexes of the invention may be linked to an enzyme capable of converting a prodrug to a drug. This allows the prodrug to be converted to the drug only at the site where it is required (i.e. targeted by the sTCR).

It is expected that the VYGFVRACL (SEQ ID NO: 1)-HLA-A24 specific TCRs disclosed herein may be used in methods for the diagnosis and treatment of cancer.

For cancer treatment, the localisation in the vicinity of tumours or metastasis would enhance the effect of toxins or immunostimulants. For vaccine delivery, the vaccine antigen could be localised in the vicinity of antigen presenting cells, thus enhancing the efficacy of the antigen. The method can also be applied for imaging purposes.

One embodiment is provided by a cell presenting a TCR of the invention. Another related embodiment is provided by a cell transfected to present a TCR of the invention. The cell presenting, or transfected to present, the TCRs of the invention may preferable be a human T cell or a human haematopoietic stem cell. Cells presenting the TCRs of the invention are useful in treatment of cancer by adoptive therapy methods. These methods provide a means of directing cells, such as T cells, to a population of target cells in a patient, said method comprising administering to a cancer patient a plurality of cells presenting TCRs of the invention that are specific for the VYGFVRACL (SEQ ID NO:1)-HLA-A24 ligand on the population of target cells.

Further embodiments of the invention are provided by a pharmaceutical composition comprising:

a TCR or a multivalent TCR complex of the invention (optionally associated with a therapeutic agent), or a plurality of cells presenting at least one TCR of the invention, or a nucleic acid or nucleic acids encoding a TCR of the invention together with a pharmaceutically acceptable carrier;

The invention also provides a method of treatment of cancer comprising administering to a subject suffering such cancer disease an effective amount of a TCR or a multivalent TCR complex of the invention (optionally associated with a therapeutic agent), or a plurality of cells presenting at least one TCR of the invention, or a nucleic acid or nucleic acids encoding a TCR of the invention. In a related embodiment the invention provides for the use of a TCR or a multivalent TCR complex of the invention (optionally associated with a therapeutic agent), or a plurality of cells presenting at least one TCR of the invention, or a nucleic acid or nucleic acids encoding a TCR of the invention in the preparation of a composition for the treatment of cancer.

Therapeutic or imaging TCRs in accordance with the invention will usually be supplied as part of a sterile, pharmaceutical composition which will normally include a pharmaceutically acceptable carrier. This pharmaceutical composition may be in any suitable form, (depending upon the desired method of administering it to a patient). It may be provided in unit dosage form, will generally be provided in a sealed container and may be provided as part of a kit. Such a kit would normally (although not necessarily) include instructions for use. It may include a plurality of said unit dosage forms.

The pharmaceutical composition may be adapted for administration by any appropriate route, for example parenteral, transdermal or via inhalation, preferably a parenteral (including subcutaneous, intramuscular, or, most preferably intravenous) route. Such compositions may be prepared by any method known in the art of pharmacy, for example by mixing the active ingredient with the carrier(s) or excipient(s) under sterile conditions.

Dosages of the substances of the present invention can vary between wide limits, depending upon the disease or disorder to be treated, the age and condition of the individual to be treated, etc. and a physician will ultimately determine appropriate dosages to be used.

Additional Aspects

A scTCR or dTCR (which preferably is constituted by constant and variable sequences corresponding to human sequences) of the present invention may be provided in substantially pure form, or as a purified or isolated preparation. For example, it may be provided in a form which is substantially free of other proteins.

High affinity TCRs having the property of specifically binding to VYGFVRACL (SEQ ID NO:1)-HLA-A*2402, and (i) comprising at least one TCR α chain variable region and/or at least one TCR β chain variable region and (ii) having a $K_D$ for the said VYGFVRACL (SEQ ID NO:1)-HLA-A*2402 complex of less than or equal to 1 μM, may be identified by a method comprising:
 (a) the production of a plurality of TCRs each comprising the α and β chain variable regions of the parental VYG-A24 TCR wherein one or both of the α and β chain variable regions comprise a mutation(s);
 (b) contacting said mutated TCRs with VYGFVRACL (SEQ ID NO:1)-HLA-A*2402 under conditions suitable to allow the binding of the TCR to VYGFVRACL (SEQ ID NO:1)-HLA-A*2402; and
 (c) measuring the $K_D$ of the interaction and selecting a TCR having the desired $K_D$.

Preferred features of each aspect of the invention are as for each of the other aspects mutatis mutandis. The prior art documents mentioned herein are incorporated to the fullest extent permitted by law.

EXAMPLES

The invention is further described in the following examples, which do not limit the scope of the invention in any way.

Reference is made in the following to the accompanying drawings in which:

FIGS. 1a and 1b provide the α chain variable region amino acid and β chain variable region amino acid sequences of the parental VYG-A24 TCR respectively.

FIGS. 2a and 2b provide respectively the DNA sequence of soluble versions of the parental VYG-A24 TCR α and β chains. The NdeI and HindIII restriction enzyme recognition sites are underlined.

FIGS. 3a and 3b provide respectively the amino acid sequences of the soluble versions of the parental VYG-A24 TCR α and β chain amino acid sequences produced from the DNA sequences of FIGS. 2a and 2b. The CDR sequences in these soluble TCR chains are underlined.

FIGS. 4a and 4b provide respectively the DNA sequence of soluble versions of the parental VYG-A24 TCR α and β chains mutated to include additional cysteine residues to form a non-native disulphide bond. The introduced cysteine codon in each chain is indicated by shading. The NdeI and HindIII restriction enzyme recognition sites are underlined.

FIGS. 5a and 5b show respectively the amino acid sequences of the soluble versions of the parental VYG-A24 TCR α and β chains produced from the DNA sequences of FIGS. 4a and 4b. The introduced cysteine in each chain is indicated by shading.

FIG. 6a provides the amino acid sequence of a truncated form of TRAC.

FIG. 6b provides the amino acid sequence of a truncated form of TRBC1.

FIG. 6c provides the amino acid sequence of a truncated form of TRBC2.

FIG. 7a provides the plasmid map of the pGMT7 plasmid.

FIG. 7b provides the DNA sequence of the pGMT7 plasmid.

FIG. 8 details the β chain amino acid sequences of the soluble disulfide-linked version of the parental VYG-A24 TCR using the TRBC2 encoded constant region fused via a peptide linker to wild-type human IL-2. The linker and IL-2 sequences are in italics.

Figure 9:
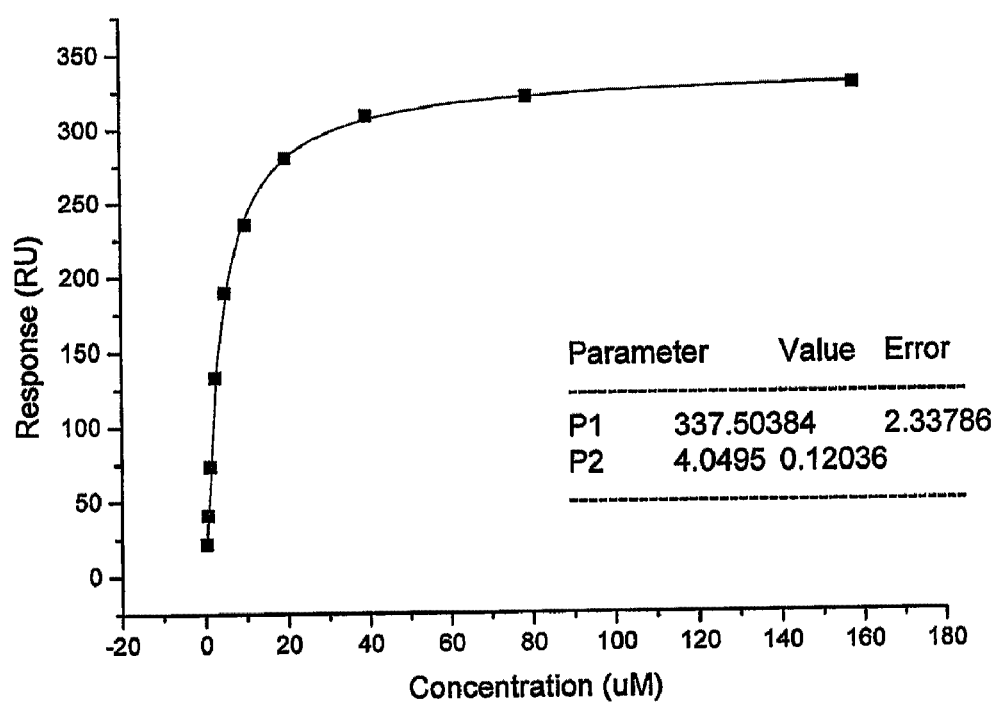

FIG. 9 provides the Biacore response curve generated for the interaction of a soluble disulfide-linked version of the parental VYG-A24 TCR and HLA-VYGFVRACL (SEQ ID NO:1)-HLA-A*2402.

FIG. 10a provides the amino acid sequence of the variable region of a (c8) VYG-A24 TCR α chain.

FIG. 10b provides the amino acid sequence of a (c8) VYG-A24 TCR α chain in a soluble form incorporating a non-native cysteine amino acid. The introduced cysteine amino acid is highlighted and the amino acids within the CDRs of this TCR chain are underlined.

Example 1

Production of a Soluble Disulfide-Linked TCR Comprising the Parental VYG-A24 Variable Regions FIGS. 4a and 4b provide the DNA sequences α and β chains of a soluble disulfide-linked form of the parental VYG-A24 TCR which is specific for the VYGFVRACL (SEQ ID NO: 1)-HLA-A*2402 complex. The β chain sequence was identified from a phage library by the method referred to in Example 6 below. The α chain is that of a known TCR specific for the ILAKFLHWL (SEQ ID NO:21)-HLA-A*0201 complex. The DNA and amino acid sequence of this α chain α was first published in WO 2005/116075. These DNA sequences can be synthesised de-novo by a number of contract research companies, for example GeneArt (Regensburg, Germany). Restriction enzyme recognition sites are also added to these DNA sequences in order to facilitate ligation of these DNA sequences into pGMT7-based expression plasmids, which contain the T7 promoter for high level expression in *E. coli* strain BL21-DE3(pLysS) (Pan et al., *Biotechniques* (2000) 29 (6): 1234-8)

The DNA sequences encoding each TCR chain cut with NdeI and HindIII are ligated into separate pGMT7 vectors, which are also cut with NdeI and HindIII. (See FIG. 7a for the plasmid map of pGMT7, and FIG. 7b for the DNA sequence of this vector (SEQ ID NO: 17)

Restriction Enzyme Recognition Sites as Introduced into DNA Encoding the Soluble Parental VYG-A24 TCR Chains:
NdeI—CATATG
HindIII—AAGCTT
Ligation Ligated plasmids are transformed into competent *E. coli* strain XL1-blue cells and plated out on LB/agar plates containing 100 mg/ml ampicillin. Following incubation overnight at 37.degree. C., single colonies are picked and grown in 10 ml LB containing 100 mg/ml ampicillin overnight at 37.degree. C. with shaking Cloned plasmids are purified using a Miniprep kit (Qiagen) and the insert is sequenced using an automated DNA sequencer (Lark Technologies).

FIGS. 5a and 5b show respectively the soluble disulfide-linked parental VYG-A24 TCR α and β chain extracellular amino acid sequences produced from the DNA sequences of FIGS. 4a and 4b.

Example 2

Production of High Affinity Variants of the Soluble Disulfide Linked VYG-A24 TCRs The soluble disulfide-linked parental VYG-A24 TCR produced as described in Example 1 can be used a template from which to produce the TCRs of the invention which have an increased affinity for the VYGFVRACL (SEQ ID NO: 43)-HLA-A*0201 complex.

As is known to those skilled in the art the necessary codon changes required to produce these mutated chains can be introduced into the DNA encoding these chains by site-directed mutagenesis. (QuickChange™ Site-Directed Mutagenesis Kit from Stratagene)

Briefly, this can be achieved by using primers that incorporate the desired codon change(s) and the pGMT7 plasmids containing the relevant parental VYG-A24 TCR chain DNA as a template for the mutagenesis:

Mutagenesis can be carried out using the following conditions: 50 ng plasmid template, 1 μl of 10 mM dNTP, 5 μl of 10.times.Pfu DNA polymerase buffer as supplied by the manufacturer, 25 pmol of fwd primer, 25 pmol of rev primer, 1 μl pfu DNA polymerase in total volume 50 μl. After an initial denaturation step of 2 mins at 95 C, the reaction can be subjected to 25 cycles of denaturation (95 C, 10 secs), annealing (55 C 10 secs), and elongation (72 C, 8 mins). The resulting product can be digested with DpnI restriction enzyme to remove the template plasmid and transformed into E. coli strain XL1-blue. Mutagenesis can be verified by sequencing.

Example 3

Expression, Refolding and Purification of Soluble TCR

The pGMT7 expression plasmids containing the parental VYG-A24 TCR α-chains and parental VYG-A24 TCR β-chains as prepared in Example 1 were transformed separately into E. coli strain BL21pLysS, and single ampicillin-resistant colonies were grown at 37° C. in TYP (ampicillin 100 μg/ml) medium to $OD_{600}$ of 0.4 before inducing protein expression with 0.5 mM IPTG. Cells were harvested three hours post-induction by centrifugation for 30 minutes at 400 rpm in a Beckman J-6B. Cell pellets were re-suspended in a buffer containing 50 mM Tris-HCl, 25% (w/v) sucrose, 1 mM NaEDTA, 0.1% (w/v) NaAzide, 10 mM DTT, pH 8.0. After an overnight freeze-thaw step, re-suspended cells were sonicated in 1 minute bursts for a total of around 10 minutes in a Milsonix XL2020 sonicator using a standard 12 mm diameter probe. Inclusion body pellets wee recovered by centrifugation for 30 minutes at 13000 rpm in a Beckman J2-21 centrifuge. Three detergent washes wee then carried out to remove cell debris and membrane components. Each time the inclusion body pellet was homogenised in a Triton buffer (50 mM Tris-HCl, 0.5% Triton-X100, 200 mM NaCl, 10 mM NaEDTA, 0.1% (w/v) NaAzide, 2 mM DTT, pH 8.0) before being pelleted by centrifugation for 15 minutes at 13000 rpm in a Beckman J2-21. Detergent and salt was then removed by a similar wash in the following buffer: 50 mM Tris-HCl, 1 mM NaEDTA, 0.1% (w/v) NaAzide, 2 mM DTT, pH 8.0. Finally, the inclusion bodies are divided into 30 mg aliquots and frozen at −70° C. Inclusion body protein yield was quantitated by solubilising with 6M guanidine-HCl and measurement with a Bradford dye-binding assay (PerBio).

Approximately 30 mg of TCR β chain and 60 mg of TCR α chain solubilised inclusion bodies were thawed from frozen stocks, samples were then mixed and the mixture diluted into 15 ml of a guanidine solution (6 M Guanidine-hydrochloride, 10 mM Sodium Acetate, 10 mM EDTA), to ensure complete chain de-naturation. The guanidine solution containing fully reduced and denatured TCR chains was then injected into 1 liter of the following refolding buffer: 100 mM Tris pH 8.5, 400 mM L-Arginine, 2 mM EDTA, 5 mM reduced Glutathione, 0.5 mM oxidised Glutathione, 5M urea, 0.2 mM PMSF. The redox couple (2-mercaptoethylamine and cystamine (to final concentrations of 6.6 mM and 3.7 mM, respectively) were added approximately 5 minutes before addition of the denatured TCR chains. The solution was left for 5 hrs .+−0.15 minutes. The refolded TCR was dialysed in Spectrapor 1 membrane (Spectrum; Product No. 132670) against 10 L 10 mM Tris pH 8.1 at 5° C.±3° C. for 18-20 hours. After this time, the dialysis buffer was changed to fresh 10 mM Tris pH 8.1 (10 L) and dialysis was continued at 5° C.±3° C. for another 20-22 hours.

sTCR was separated from degradation products and impurities by loading the dialysed refold onto a POROS 50HQ anion exchange column and eluting bound protein with a gradient of 0-500 mM NaCl over 50 column volumes using an Akta purifier (Pharmacia). Peak fractions were stored at 4.degree. C. and analysed by Coomassie-stained SDS-PAGE before being pooled and concentrated. Finally, the sTCR was purified and characterised using a Superdex 200HR gel filtration column pre-equilibrated in HBS-EP buffer (10 mM HEPES pH 7.4, 150 mM NaCl, 3.5 mM EDTA, 0.05% nonidet p40). The peak eluting at a relative molecular weight of approximately 50 kDa was pooled and concentrated prior to characterisation by BIAcore surface plasmon resonance analysis.

Example 4

Biacore Surface Plasmon Resonance Characterisation of sTCR Binding to Specific pMHC A surface plasmon resonance biosensor (Biacore 3000™) was used to analyse the binding of parental VYG-A24 TCR to VYGFVRACL (SEQ ID NO:1)-HLA-A*2402. This was facilitated by producing single VYGFVRACL (SEQ ID NO:1)-HLA-A*2402 complexes (described below) which were immobilised to a streptavidin-coated binding surface in a semi-oriented fashion, allowing efficient testing of the binding of a soluble T-cell receptor to up to four different pMHC (immobilised on separate flow cells) simultaneously. Manual injection of HLA complex allows the precise level of immobilised class I molecules to be manipulated easily.

Biotinylated class I HLA-A*2402 molecules were refolded in vitro from bacterially-expressed inclusion bodies containing the constituent subunit proteins and synthetic peptide, followed by purification and in vitro enzymatic biotinylation (O'Callaghan et al. (1999) *Anal. Biochem.* 266: 9-15). HLA-A*2402-heavy chain was expressed with a C-terminal biotinylation tag which replaces the transmembrane and cytoplasmic domains of the protein in an appropriate construct. Inclusion body expression levels of .about.75 mg/liter bacterial culture were obtained. The MHC light-chain or β2-microglobulin was also expressed as inclusion bodies in E. coli from an appropriate construct, at a level of 500 mg/liter bacterial culture.

E. coli cells were lysed and inclusion bodies are purified to approximately 80% purity. Protein from inclusion bodies was denatured in 6 M guanidine-HCl, 50 mM Tris pH 8.1, 100 mM NaCl, 10 mM DTT, 10 mM EDTA, and was refolded at a concentration of 30 mg/liter heavy chain, 30 mg/liter β2 m into 0.4 M L-Arginine-HCl, 100 mM Tris pH 8.1, 3.7 mM cystamine, 6.6 mM β-cysteamine, 4 mg/ml of the VYGFVR-ACL (SEQ ID NO:1) peptide required to be loaded by the HLA-A*0201 molecule, by addition of a single pulse of denatured protein into refold buffer at <5° C. Refolding was allowed to reach completion at 4° C. for at least 1 hour.

Buffer was exchanged by dialysis in 10 volumes of 10 mM Tris pH 8.1. Two changes of buffer were necessary to reduce the ionic strength of the solution sufficiently. The protein solution was then filtered through a 1.5 μm cellulose acetate filter and loaded onto a POROS 50HQ anion exchange column (8 ml bed volume). Protein was eluted with a linear 0-500 mM NaCl gradient. HLA-A*0201-peptide complex eluted at approximately 250 mM NaCl, and peak fractions were collected, a cocktail of protease inhibitors (Calbiochem) was added and the fractions were chilled on ice.

Biotinylation tagged pMHC molecules were buffer exchanged into 10 mM Tris pH 8.1, 5 mM NaCl using a Pharmacia fast desalting column equilibrated in the same buffer. Immediately upon elution, the protein-containing fractions were chilled on ice and protease inhibitor cocktail (Calbiochem) was added. Biotinylation reagents were then added: 1 mM biotin, 5 mM ATP (buffered to pH 8), 7.5 mM MgCl2, and 5 μg/mlBirA enzyme (purified according to O'Callaghan et al. (1999) *Anal. Biochem.* 266: 9-15). The mixture was then allowed to incubate at room temperature overnight.

The biotinylated pHLA-A*2402 molecules were purified using gel filtration chromatography. A Pharmacia Superdex 75 HR 10/30 column was pre-equilibrated with filtered PBS and 1 ml of the biotinylation reaction mixture was loaded and the column was developed with PBS at 0.5 ml/min. Biotinylated pHLA-A*0201 molecules eluted as a single peak at approximately 15 ml. Fractions containing protein were pooled, chilled on ice, and protease inhibitor cocktail was added. Protein concentration was determined using a Coomassie-binding assay (PerBio) and aliquots of biotinylated VYGFVRACL (SEQ ID NO:1)-HLA-A*2402 molecules were stored frozen at −20° C. Streptavidin was immobilised by standard amine coupling methods.

Such immobilised complexes are capable of binding both T-cell receptors and the coreceptor CD8αα, both of which may be injected in the soluble phase. Specific binding of TCR is obtained even at low concentrations (at least 40 μg/ml), implying the TCR is relatively stable. The pMHC binding properties of sTCR are observed to be qualitatively and quantitatively similar if sTCR is used either in the soluble or immobilised phase. This is an important control for partial activity of soluble species and also suggests that biotinylated pMHC complexes are biologically as active as non-biotinylated complexes.

The interactions between the soluble parental VYG-A24 TCRs containing a novel inter-chain bond and its cognate pMHC or an irrelevant pMHC combination, the production of which is described above, were analysed on a Biacore 3000™ surface plasmon resonance (SPR) biosensor. SPR measures changes in refractive index expressed in response units (RU) near a sensor surface within a small flow cell, a principle that can be used to detect receptor ligand interactions and to analyse their affinity and kinetic parameters. The probe flow cells were prepared by immobilising the individual HLA-peptide complexes in separate flow cells via binding between the biotin cross linked onto β2 m and streptavidin which have been chemically cross linked to the activated surface of the flow cells. The assay was then performed by passing sTCR over the surfaces of the different flow cells at a constant flow rate, measuring the SPR response in doing so.

To Measure Equilibrium Binding Constant

Serial dilutions of the parental VYG-A24 TCR were prepared and injected at constant flow rate of 5 μl min-1 over two different flow cells; one coated with ~1000 RU of specific VYGFVRACL (SEQ ID NO:1)-HLA-A*2402 complex, the second coated with ~1000 RU of non-specific HLA-A24-peptide complex. Response was normalised for each concentration using the measurement from the control cell. Normalised data response was plotted versus concentration of TCR sample and fitted to a hyperbola in order to calculate the equilibrium binding constant, $K_D$. (Price & Dwek, *Principles and Problems in Physical Chemistry for Biochemists* ($2^{nd}$ Edition) 1979, Clarendon Press, Oxford).

To Measure Kinetic Parameters

For high affinity TCRs $K_D$ can be determined by experimentally measuring the dissociation rate constant, kd, and the association rate constant, ka. The equilibrium constant $K_D$ was calculated as kd/ka. TCR can be injected over two different cells one coated with ~300 RU of specific HLA-A*2402-VYGFVRACL (SEQ ID NO:1) complex, the second coated with ~300 RU of a non-specific peptide-HLA complex. Flow rate is set at 50 μl/min. Typically 250 μl of TCR at ~3 μM concentration are injected. Buffer is then flowed over until the response returns to baseline. Kinetic parameters are calculated using Biaevaluation software. The dissociation phase is also fitted to a single exponential decay equation enabling calculation of half-life.

Results

The interaction between a soluble disulfide-linked parental VYG-A24 TCR (consisting of the soluble disulfide-linked α and β TCR chains detailed in SEQ ID Nos: 15 and 16 respectively) and the VYGFVRACL (SEQ ID NO:1)-HLA-A*2402 complex was analysed using the above methods and demonstrated a $K_D$ of 4 μM. (See FIG. 9 for Biacore response curve)

Example 5

Production of a Soluble VYG-A24 TCR-WT Human IL-2 Fusion Protein

The methods substantially as described in Examples 1 to 3 can be used to produce a soluble VYG-A24 TCR-WT human IL-2 fusion protein. Briefly, the DNA encoding the desired linker and WT human IL-2 are added into the 3' end of the DNA sequence of the soluble disulfide-linked VYG-A24 TCR β chain. FIG. 8 provides the amino acid sequence of a fusion protein comprising a disulfide-linked parental VYG-A24 TCR β chain fused to WT human IL-2 via linker sequence. (SEQ ID NO: 18) The linker and IL-2 portion of this fusion protein are indicated in italics and the introduced cysteine residue in the TCR β is indicated by shading. The DNA encoding this construct can then be ligated into pGMT7. The soluble parental VYG-A24 TCR-IL-2 fusion protein can then be expressed by combining this β chain fusion protein with the soluble disulfide-linked parental VYG-A24 TCR α chain detailed in FIG. 5a (SEQ ID NO: 15) using the methods substantially as described in Example 3.

Example 6

Isolation of an HLA-A24-VYGFVRACL (SEQ ID NO:1) Binding TCR from an A6 TCR-Derived Phage Display Library A phage displayed TCR library was created using the procedures described in WO 2004/044004. Briefly, the library was based on a soluble disulfide-linked A6 TCR specific for HLA-A2-LLFGYPVYV (SEQ ID NO:22). The diversity of the A6 TCR library was created by using mutagenic primers which introduced mutations in the CDR3 regions of the displayed A6 TCRs. In order to display the A6 TCR library phagemid vectors were constructed for expression of fusion proteins comprising the heterodimeric A6 TCR containing a non-native disulfide inter-chain bond with the gill phage coat protein. *E. coli* XL-1-Blue cells containing a phagemid encoding the soluble A6 TCR α chain and an A6 TCR β chain fused to the phage gIII protein were used to express the phage displayed TCRs. The presence of functional VYGFVRACL (SEQ ID NO:1)-HLA-A*2402 binding TCRs displayed on the phage particles were detected using a phage ELISA method, The DNA encoding the phage-displayed TCRs which were selected by the ELISA was then used to construct soluble disulfide-linked TCRs. The binding of these soluble TCRs to HLA-A24-VYGFVRACL (SEQ ID NO:1) was then assessed using the Biacore method of Example 4 herein. The soluble disulfide-linked parental VYG-A24 TCR was constructed using a TCR β chain isolated from this library (SEQ ID NO; 16) associated with a soluble disulfide-linked analogue of a "wild-type" ILAKFLHWL (SEQ ID NO:21)-HLA-A*0201 binding TCR α Chain (SEQ ID NO: 15). The TCR α chain shown in FIG. 10*b* (SEQ ID NO: 20) was also isolated from this library, displayed as an αβ TCR specific for the VYGFVRACL (SEQ ID NO:1)-HLA-A*2402 complex, in combination with the TCR β chain shown in FIG. 5*b* (SEQ ID NO 16).

The invention claimed is:

1. An isolated T cell receptor (TCR) having the property of specifically binding to VYGFVRACL (SEQ ID NO:1)-HLA-A24 selected from the group consisting of TCRs which comprise:

SEQ ID NO: 2 and SEQ ID NO: 3;
SEQ ID NO:19 and SEQ ID NO:3;
SEQ ID NO:15 and SEQ ID NO:16; and
SEQ ID NO:20 and SEQ ID NO:16.

* * * * *